US011152081B2

(12) United States Patent
Lario et al.

(10) Patent No.: US 11,152,081 B2
(45) Date of Patent: Oct. 19, 2021

(54) METHODS FOR DETERMINING CORRELATED RESIDUES IN A PROTEIN OR OTHER BIOPOLYMER USING MOLECULAR DYNAMICS

(71) Applicant: ZYMEWORKS INC., Vancouver (CA)

(72) Inventors: Paula I. Lario, Vancouver (CA); Johannes Mullegger, Vancouver (CA); Surjit B. Dixit, Richmond (CA); Tomas Rodinger, Vancouver (CA); Powell Patrick Cheng Tan, Vancouver (CA)

(73) Assignee: ZYMEWORKS INC., Vancouver (CA)

( * ) Notice: Subject to any disclaimer, the term of this patent is extended or adjusted under 35 U.S.C. 154(b) by 961 days.

(21) Appl. No.: 15/221,379

(22) Filed: Jul. 27, 2016

(65) Prior Publication Data
US 2017/0053063 A1    Feb. 23, 2017

Related U.S. Application Data

(62) Division of application No. 12/866,437, filed as application No. PCT/IB2009/005040 on Feb. 5, 2009, now Pat. No. 9,404,928.
(Continued)

(51) Int. Cl.
    *G01N 33/48*   (2006.01)
    *G01N 33/50*   (2006.01)
(Continued)

(52) U.S. Cl.
    CPC ............ *G16B 40/00* (2019.02); *G16B 45/00* (2019.02)

(58) Field of Classification Search
    CPC .......... G16B 40/00; G16B 5/00; G16B 15/00; G16B 45/00
    See application file for complete search history.

(56) References Cited

U.S. PATENT DOCUMENTS

| 4,795,805 A | 1/1989 | Itoh et al. |
| 6,014,449 A | 1/2000 | Jacobs et al. |
| (Continued) | | |

FOREIGN PATENT DOCUMENTS

| EP | 1199669 A2 | 4/2002 |
| EP | 1724697 A1 | 11/2006 |
| (Continued) | | |

OTHER PUBLICATIONS

Cornilescu et al. Protein backbone angle restraints from searching a database for chemical shift and sequence homology. Journal of Biomolecular NMR, vol. 13, pp. 289-302. (Year: 1999).*
(Continued)

*Primary Examiner* — Russell S Negin
(74) *Attorney, Agent, or Firm* — Morgan, Lewis & Bockius LLP; Brett Lovejoy

(57) ABSTRACT

The invention provides methods and systems of determining biopolymer profiles and correlations between structural units (residues) of a biopolymer based on sampling of the conformational space available to the molecule. The correlations between these structural units can further be used to find networks within a biopolymer such as the coupled residue networks in a protein. The invention also provides for designing and engineering biopolymers including polypeptides, nucleic acids and carbohydrates using the information derived from the conformation clustering and subsequent methods described herein.

7 Claims, 15 Drawing Sheets
(13 of 15 Drawing Sheet(s) Filed in Color)

Related U.S. Application Data

(60) Provisional application No. 61/026,435, filed on Feb. 5, 2008, provisional application No. 61/116,267, filed on Nov. 19, 2008.

(51) Int. Cl.
  *G16B 40/00* (2019.01)
  *G16B 45/00* (2019.01)

(56) References Cited

U.S. PATENT DOCUMENTS

| | | | | |
|---|---|---|---|---|
| 2001/0051855 A1* | 12/2001 | Wang | .................. | G06F 19/16 702/19 |
| 2003/0021687 A1 | 11/2003 | Campbell et al. | | |
| 2005/0119837 A1* | 6/2005 | Prakash | .................. | G06F 19/28 702/27 |
| 2005/0136481 A1 | 6/2005 | Trabanino et al. | | |

FOREIGN PATENT DOCUMENTS

| | | |
|---|---|---|
| JP | 2005-242493 A | 9/2005 |
| WO | WO 2005/083616 | 9/2005 |

OTHER PUBLICATIONS

Karplus et al. Molecular dynamics simulations in biology. Nature, vol. 347, pp. 631-639. (Year: 1990).*

Variance. In G. Bannock, R.E. Baxter, & E. Davis, The Penguin Dictionary of Economics (7th ed). London, UK: Penguin. Retrieved online on Jul. 29, 2018. (Year: 2003).*

Beroza et al., "Protonation of interacting residues in a protein by a Monte Carlo method: application to lysozyme and the photosynthetic reaction center of Rhodobacter sphaeroides." PNAS, vol. 88, pp. 5804-5808 (1991).

Bravi et al., "SONHICA (Simple Optimized Non-Hierarchical Cluster Analysis): A New Tool for Analysis of Molecular Conformations", Journal of Computational Chemistry, vol. 18, No. 10, pp. 1295-1311 (1997).

Brooks et al., "CHARMM: A Program for macromolecular energy, minimization, and dynamics calculations." Journal of Computational Chemistry, vol. 4, pp. 187-217 (1983).

Davis et al., "The Backrub Motion: How Protein Backbone Shurgs When a Sidechain Dances", Structure, vol. 14, pp. 265-274 (2006).

Delaglio et al., "Measurement of homonuclear proton couplings from regular 2D COSY spectra." Journal of Magnetic Resonance, vol. 149, pp. 276-281 (2001).

DeMaeyer et al., "All in one: a highly detailed rotamer library improves both accuracy and speed in the modelling of sidechains by dead-end elimination", Folding and Design, vol. 2, No. 1, pp. 53-65 (1997).

Desmet et al., "The dead-end elimination theorem and its use in protein side-chain positioning", Nature, vol. 356, pp. 539-542 (1992).

Dunbrack and Cohen, "Bayesian statistical analysis of protein side-chain rotamer preferences", Protein Science, vol. 6, pp. 1661-1681 (1997).

Fitzgerald et al., "Polypeptide Motions Are Dominated by Peptide Group Oscillations Resulting from Dihedral Angle Correlations between Nearest Neighbors", Biochemistry, vol. 46, pp. 669-682 (2007).

Harte et al., "Domain communication in the dynamical structure of human immunodeficiency virus 1 protease", PNAS, vol. 87, pp. 8864-8868 (1990).

Ichiye et al., "Collective Motions in Proteins: A Covariance Analysis of Atomic Fluctuations in Molecular Dynamics and Normal Mode Simulations", PROTEINS: Structure, Function, and Genetics, vol. 11, pp. 205-217 (1991).

Kandiraju et al., "Dihedral Angle based Dimensionality Reduction for Protein Structural Comparison", Proceedings of the International Conference on Information Technology: Coding and Computing, vol. 1, pp. 14-19 (2005).

Kishan, K.V. Radha, "Structural Biology, Protein Conformations and Drug Designing", Current Protein and Peptide Science, vol. 8, pp. 376-308 (2007).

Lovell et al., "The Penultimate Rotamer Library", PROTEINS: Structure, Function, and Genetics, vol. 40, pp. 389-408 (2000).

Matthews, "Structural and genetic analysis of the folding and function of T4 lysozyme", FASEB J., vol. 10, pp. 35-41 (1996).

Petrellas and Karplus, "The Energentics of Off-rotamer Protein Side-chain Conformations", Journal of Molecular Biology, vol. 312, pp. 1161-1175 (2001).

Ponder and Richards, "Tertiary Templates for Proteins", Journal of Molecular Biology, vol. 193, pp. 775-791 (1987).

Stawiski et al., "Predicting protein function from structure: Unique structural features of proteases", PNAS, vol. 97, No. 8, pp. 3954-3958 (2000).

Tester et al., "Thermodynamics and its Applications", 3rd Ed., Prentice Hall PTR: Upper Saddle River, New Jersey, pp. 441-447 (1997).

Tuffery et al., "A New Approach to the Rapid Determination of Protein Side Chain Conformations", Journal of Biomolecular Structure & Dynamics, vol. 8, No. 6, pp. 1267-1289 (1991).

Brissos et al., "Improving activity and stability of cutinase towards the anionic detergent AOT by complete saturation mutagenesis." Protein Engineering, Design & Selection. vol. 21, No. 6, pp. 387-393 (2008).

* cited by examiner

Definition of "elevation" and "azimuth" angles between two planes

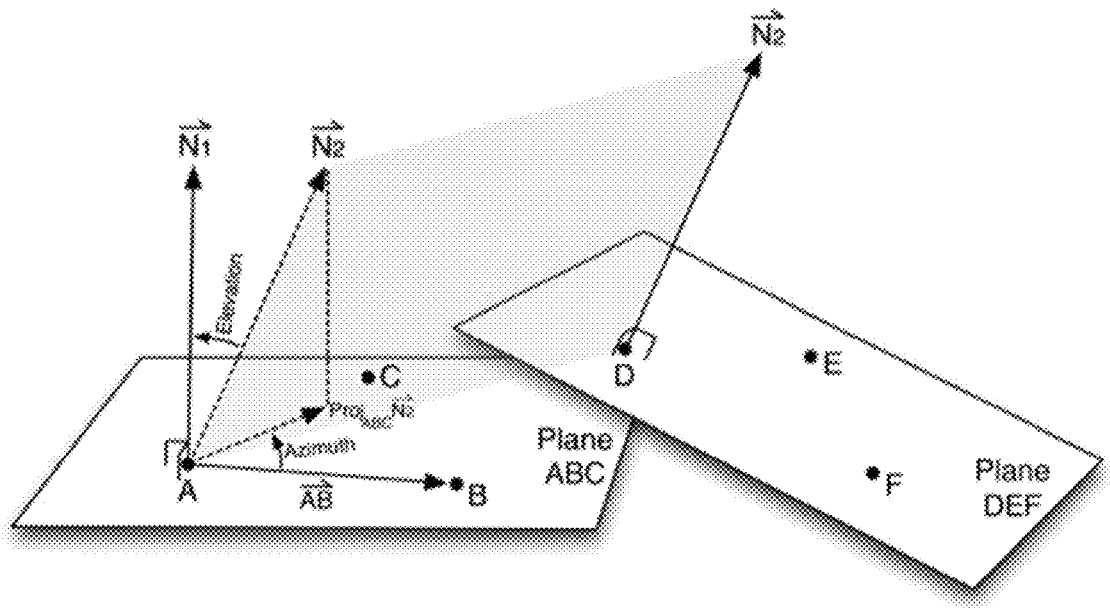

Definitions:
Plane ABC passes through atoms A, B, and C.
Plane DEF passes through atoms D, E, and F.
Vector N1 is normal to plane ABC.
Vector N2 is normal to plane DEF.
Vector AB is the vector pointing from atom A to atom B.
Elevation is the angle between vectors N1 and N2.
Azimuth is the angle between the projection of vector N2 onto plane ABC and vector AB.

Figure 1

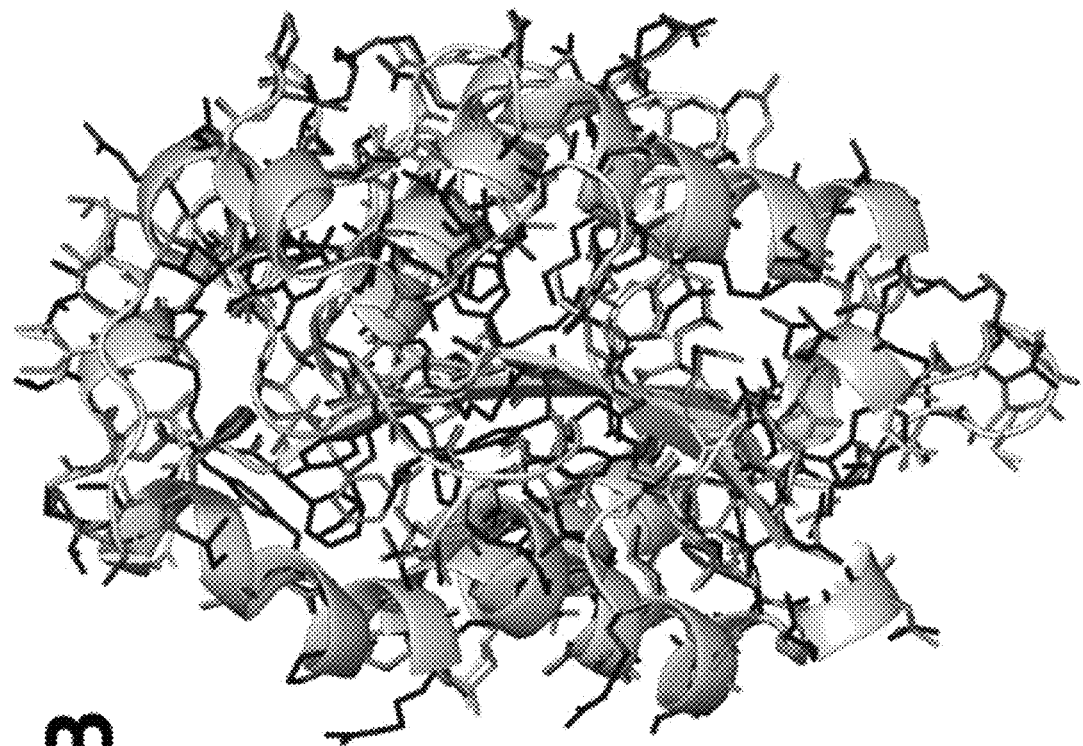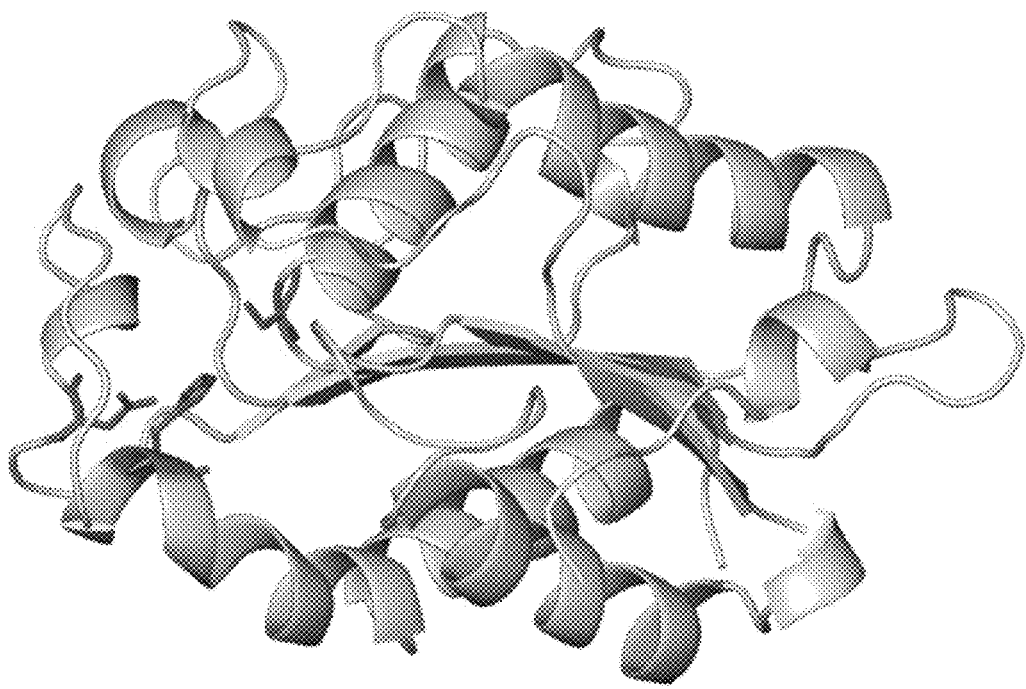
Figure 5

METHODS FOR DETERMINING CORRELATED RESIDUES IN A PROTEIN OR OTHER BIOPOLYMER USING MOLECULAR DYNAMICS

CROSS-REFERENCE TO RELATED APPLICATIONS

This application is a Divisional of U.S. application Ser. No. 12/866,437 filed Oct. 11, 2010, now U.S. Pat. No. 9,404,928, which is a 371 U.S. National Phase application of PCT/IB2009/005040 filed Feb. 5, 2009 which claims the benefit under 35 U.S.C. §119(e) of U.S. Provisional Application No. 61/026,435, filed Feb. 5, 2008; and 61/116,267, filed Nov. 19, 2008, which are all incorporated by reference in their entirety for all purposes.

BACKGROUND OF THE INVENTION

One of the most challenging aspects of enzyme engineering is deducing the correlations between the residues of a protein. Previous methods to find correlations between residues investigated the collective motion of protein residues and have relied on principle component analysis, in which a covariance matrix is evaluated. Such methods are of limited usefulness, as they identify correlated residue movements only in the same (parallel) or opposite (anti-parallel) direction. These previous methods are also hampered by having low sensitivity for identifying correlated residue networks (Harte, W. E., et. al., 1990, PNAS, 85, 4686; Ichiye, T. and Karplus, M., 1991, Protein Struct. Funct. Genet. 11:205).

Other methods to find correlations between residues in a protein use bioinformatics based approaches (for example Fodor et. al., 2004, *Proteins*, 56,211 and citations therein). These methods rely on the analysis of large sequence alignments and statistical analysis of correlated mutations. However, it has been shown that statistical coupling between two positions in a protein based on sequence alignments is not necessarily reflected in actual thermodynamic coupling as determined experimentally using double mutant cycles (Chi et. al., 2008, *PNAS*, 105,12).

SUMMARY OF THE INVENTION

Presented herein are unique methods of deducing networks of residues that exhibit related movements within a protein or the network of component structural units within a biopolymer. The present methods for identifying residue networks with correlated motions have high enough sensitivity to detect even subtle off-rotamer conformations. These off-rotamer conformations are often found in conformers of apo- and complexed proteins.

In a molecular dynamics or Monte Carlo simulation, a variety of metrics are used to analyze the local protein or biopolymer geometry. The results of the simulation are then used to identify the various alternate conformations of the residues within the biopolymer in the sampled time frame. The interrelatedness of these alternate conformations is used to establish networks of correlated motions. The present analysis takes advantage of the fact that in a vast majority of cases, available alternate residue conformations are very few in number.

The high sensitivity of the presented methods makes them suitable for deducing the structure/activity relationships in a wide variety of applications. For example, the analysis results can be used to intelligently select key residues of a polypeptide to be used in saturated mutagenesis techniques. Furthermore, a deep understanding of the dynamic networks in a protein is essential for accuracy in predictive in silico experiments such as homology modeling, docking studies, and quantum mechanical/molecular mechanical simulations. By identifying the more probable conformational states and the temporal relationships between such conformations, it becomes possible to identify the more rigid structural conformations that are likely to play key roles in the stability and function of a biopolymer. The methods provided herein can be used to provide various types information relating to a biopolymer. Such information includes, for example, biopolymer profiles, profiles of the structural units of the biopolymer, conformational states of the biopolymer or of the structural subunits of the biopolymer, and correlations between various structural subunits, as discussed herein. In various exemplary embodiments, the biopolymer is a polypeptide, and the structural subunit is an amino acid.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 illustrates the elevation and azimuth angles that are calculated between two planes, each in turn defined by three atomic positions.

FIG. 5 shows the 3-dimensional representative residue structures for each of the defined residue conformations mapped onto a template backbone structure. Details are provided in the examples section.

DETAILED DESCRIPTION OF THE INVENTION

Figure 2:
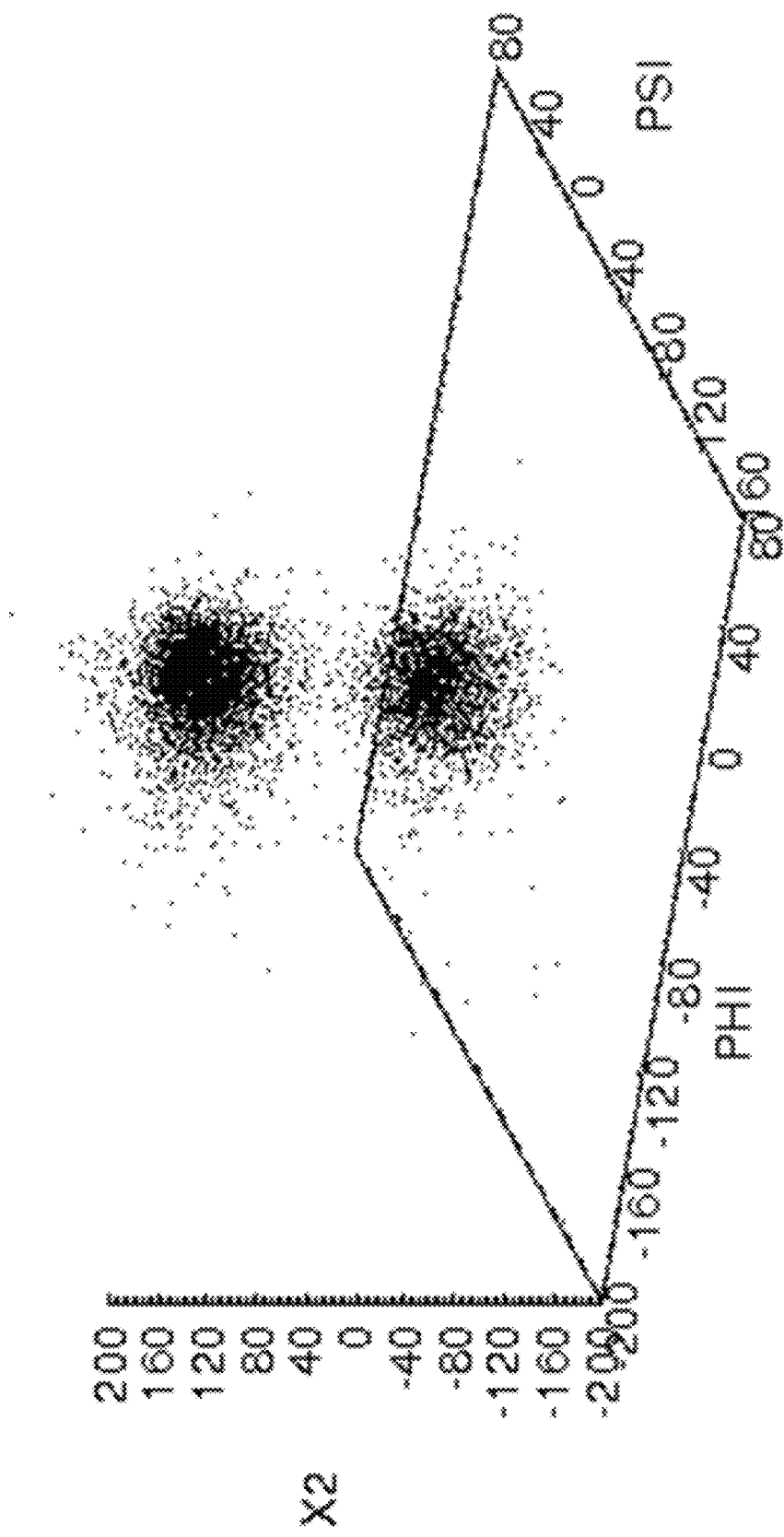
FIG. 2 shows a scatter-plot of geometric metric data from a molecular dynamics simulation. Data points represent a particular structural snapshot or frame in the trajectory, and the position of this data point is bound by the three angles plotted with respect to each other. Here the data separate in two distinct clusters. Clustering is performed on all available angles, or a subset thereof, however only three dimensions can be visually depicted with any clarity (as shown here).

Definitions: The term geometric metrics describes the plurality of measurable physical attributes of a structural unit or residue (used interchangeably herein) of a biopolymer, an amino acid in the case of a protein. Geometric metrics can be defined either by 1) dihedral, plane or other measurable angles as defined by the atoms of the respective residue, 2) distances between atoms of the same residue or to atoms of another residue, and/or 3) distance between atoms of the same residue and a reference atom or position in the structure. A residue population is the sum of all snapshots or samples obtained for a single residue. The population would normally be equal to the number of frames captured in a molecular dynamics simulation or the number of samples taken from a Monte Carlo simulation. A residue conformation is defined in terms of the observed combination of geometric metrics attributed to a particular residue structure. A residue cluster refers to the plurality of snapshots, which have been assigned the same conformation, based on clustering all or a part of the defined geometric metrics. A conformational frequency refers to the number of frames which have been assigned the same residue conformation. Simulation refers to the process of conformational sampling, performed either by either molecular dynamics or a Monte Carlo based sampling approach. A trajectory contains the conformational frames produced by a simulation. Graph theory refers to the term as used in mathematics and computer science (for example, see Reinhard Diestel, Graph Theory; Edition 3, Springer 2005). The term clustering tools refers to the plurality of mathematical methods and algorithms and programs which implement those, that can be used to identify clusters of similar data points from data sets. The term Dynamical Cross Correlation Method refers to a graphical representation of the cross correlation matrix of atomic displacements of a molecular structure in a molecular dynamics trajectory with reference to another conformational state of that structure. Normal mode analysis is the study of characteristic harmonic vibrations and frequencies about a local energy minimum of a molecular system. Elastic network model refers to the representation of a protein structure as comprising of a network of harmonic springs approximating the interaction between residue pairs.

Amino acids within a protein generally have access to a limited conformational space because of steric and dihedral constraints within the protein structure. This is particularly true for buried residues as well as those present in concave areas on the surface of proteins where active sites can exist. Thus, a limited number of probable alternate residue conformations are available in a protein structure. The extent and nature of amino acid rotamer conformations observed in library of protein structure has been studied in the literature (such as the Dunbrak library: http://dunbrack.fccc.edu/bb-dep/index.php, or other published libraries: see for example, Lovel et al., 2000, *Proteins: Structure Function and Genetics* 40, 389; Dunbrack & Cohen, 1997, *Protein Science*, 6, 1661; DeMaeyer et al., 1997, *Folding and Design*, 2, 53; Tuffery et al., 1991, *Journal of Biomolecular Structure and Dynamics*, 8, 1267; and Ponder & Richards, 1987, *Journal of Molecular Biology*, 193, 775). In the present work only rotamers or off-rotamer conformations that are observed in the simulation of the protein under study will be included in the cross correlation analysis instead of considering the large number of potential rotamers that are observed in a library of protein structures. In fact, it is usually the changes in off-rotamer conformations that are important in residue conduits/networks in a protein. The present techniques allow for the identification of subtle off-rotamer conformations that are often associated with critical roles in binding interactions and enzyme mechanisms. Off-rotamer conformations include, for example, the strained rack conformations, i.e., conformers sampled through rocking motions of the residue (Davis et al., 2006, *Structure* 14, 265). By including off-rotamer conformations, the level of sensitivity required to accurately define correlated residue networks is achieved.

As used herein, "polypeptide" means two or more amino acids or residues linked by a peptide bond. "Polypeptide" and "protein" are interchangeable and include oligopeptides and peptides.

For a single amino acid an "off-rotamer" or "nonrotameric" sidechain position has a higher internal energy than some "on-rotamer" or "rotamer" position. The sterics of sidechain heteroatoms tend to constrain sidechain dihedral angles $\chi$ to certain regions in phase space. $\chi$ about bonds involving a tetrahedral carbon tend to be at energetic minima at $-60°$, $180°$, and $60°$, for example. (Petrella & Karplus, 2001, *Journal of Molecular Biology*, 312, 1161). As a nonlimiting example, allowing for statistical variations, one could consider on-rotamer positions to fall within the ranges $\{30\text{-}90°, 150\text{-}210°, 270\text{-}330°\}$. In this case, off-rotamer positions could be considered as those found in the ranges $\{90\text{-}150°, 210\text{-}270°, 330\text{-}30°\}$. Thus, an off-rotamer position is relative to an on-rotamer or rotamer position, which is determined by setting a statistically appropriate range about some energetic minimum in phase space. Useful ranges include $\pm 10°$, $\pm 20°$ and $\pm 30°$. Ranges for on- and off-rotamers can be found accordingly for other residue metrics additional to the classically defined $\chi$ angels. Because they are typically less energetically favorable relative to on-rotamers, off-rotamers are less likely to be found in a protein structure. Nevertheless, due to the surrounding polypeptide environment the energetic landscape of an amino acid in a polypeptide is different from that of the individual residue. The unique local environment of an amino acid in a polypeptide, can lead to "off-rotamer" positions that represent local energetic minima. Structural characterization of the side-chain geometries, both "off-rotamer" or "on-rotamer", that are physically distinct and populated, must be taken into account to ensure accurate results.

Generally, the present methods provide the means to acquire the appropriate data concerning the residues of a biopolymer and analyze the data to determine correlated motions between them.

Geometric data concerning residue conformations for a biopolymer can be generated by performing molecular dynamics (MD) simulations. In an MD simulation, a molecule subjected to an energy potential evolves over time according to solutions of Newton's equations of motion. The potential energy of the molecule is calculated using a function that includes terms relating to the various relationships between the parts of a protein. Thus, terms may be used to account for energy due to, for example, bond length, bond angle, and dihedral angles, as well as nonbonding interactions such as Coulombic and Lennard-Jones interactions. Cross or other higher order terms may also be useful. While such a potential energy is useful for modeling proteins, nucleic acids, lipids and carbohydrates, analogous functions can be chosen for other types of molecules such as small organic molecules.

Taking the gradient of the potential energy function with respect to the position of an atom results in an equation for the force on the atom. Newton's equation of motion for the atom is solved using the calculated force, and the results are used to move the atom through space. Methods for solving the equation of motion include any useful numerical algorithm, such as the Verlet algorithm.

Thus, any MD simulation capable of evolving the biomolecule along an MD trajectory may be used in the present invention. For example, MD trajectories could be calculated using CHARMM, AMBER, GROMACS, and NAMD software packages. See generally Adcock & McCammon, 2006, *Chemical Reviews*, 106, 1589.

In one embodiment, the data concerning polypeptide residues metrics can also be generated by performing Monte Carlo sampling of the protein sidechain conformations. In this approach, randomly selected torsion (dihedral) angles in the amino acid side chain are randomly perturbed. The move is accepted if it is energetically more favorable than the value of the angle prior to the perturbation. In case the move is energetically unfavorable, it is accepted with a probability defined by Boltzmann statistics and rejected in all other cases. The algorithm is followed iteratively to generate an ensemble of conformations.

In one embodiment, the data concerning the polypeptide residue metrics can be generated by performing Monte Carlo sampling of both the protein side chain and backbone conformations.

In principle, any other method capable of creating a large enough sample describing the conformational space accessible to the protein of interest can be used, that would for example include NMR methods or high throughput high resolution methods including Laue X-ray crystallography.

In one embodiment, analysis of simulation data involves defining residue clusters for each separate residue metric, calculating the cluster frequency of each cluster and then further analyzing the cluster frequencies. In another embodiment, analysis of simulation data involves defining residue clusters based on a plurality of residue metrics, calculating the cluster frequency of each residue cluster and then further analyzing the cluster frequencies.

A simple and robust way to screen for alternate residue conformations is to use residue metrics n to sample positional differences relative to the framework of each residue X. Useful residue metrics include the standard bond torsion angles of residues, terminal atom positions, and a unique set of angles defined to increase the sensitivity of the sampling.

In one aspect, the invention provides for a method of defining an angle metric. One such angle metric, which can be uniquely defined for each residue type, is referred to herein as a "plane angle metric" and can be useful for the sensitive detection of distinct strained or tilted alternate geometries that can occur for residues including glycine and alanine. One advantage for providing such a metric is to increase sampling sensitivity during a simulation. In other words, these plane angles allow for the resolution of two close but structurally distinct alternate conformations that are separated by an energetically less favorable barrier. A set of plane angle metrics can be determined by defining two different planes that are defined by two different sets of atoms and then calculating both the elevation and azimuth angles between these planes (see FIG. 1 for illustration). For example, in alanine, the elevation plane angle can be defined by the angle between a first plane defined by the atoms $C^\alpha$, $C^o$ and N of the residue backbone and a second plane defined by $C^\beta$, $C^o$ and N, which includes both backbone and terminal atoms. Thus, a plane that is used to define in part a plane angle can be defined using three atoms independently chosen from the backbone and terminal atoms in any combination.

With two plane so defined, the elevation plane angle metric can be calculated using a normal vector of each plane. Referring to FIG. 1, where $N_1$ and $N_2$ are the normal vectors of two different plane angles, the plane angle metric can be determined according to the equation $N_1 \cdot N_2 = |N_1||N_2| \cos \theta$.

With two planes so defined, the azimuth plane angle metric can be calculated using a normal vector of the second plane projected onto the first plane and calculating the angle between that vector and the vector defined by the first two atoms in the first plane (see FIG. 1). Where $N_2$ is the normal vector of the second plane and AB is the vector between atoms A and B in the first plane.

Table 1 shows examples of atoms that can be used to define a plane angle metric for various amino acids.

TABLE 1

| Amino Acid | Plane 1 | Plane 2 |
|---|---|---|
| Gly | N, CA, C | N, CA, O |
| Gly | N, CA, C | N, C, O |
| Gly | CA, C, O | N, CA, O |
| Gly | CA, C, O | N, C, O |
| Ala | N, CA, C | N, CB, C |
| Ala | N, CA, C | CB, CA, C |
| Ala | CA, C, O | N, CB, C |
| Ala | CA, C, O | CB, CA, C |
| Val | N, CA, C | CA, CB, CG2 |
| Val | N, CA, C | CB, CG1, CG2 |
| Val | CA, C, O | CA, CB, CG2 |
| Val | CA, C, O | CB, CG1, CG2 |
| Leu | N, CA, C | CA, CB, CD2 |
| Leu | N, CA, C | CB, CD1, CD2 |
| Leu | CA, C, O | CA, CB, CD2 |
| Leu | CA, C, O | CB, CD1, CD2 |
| Ile | N, CA, C | CA, CB, CD1 |
| Ile | N, CA, C | CB, CG2, CD1 |
| Ile | CA, C, O | CA, CB, CD1 |
| Ile | CA, C, O | CB, CG2, CD1 |
| Ser | N, CA, C | CA, CB, OG |
| Ser | N, CA, C | N, OG, C |
| Ser | CA, C, O | CA, CB, OG |
| Ser | CA, C, O | N, OG, C |
| Thr | N, CA, C | CA, CB, OG1 |
| Thr | N, CA, C | CB, CG2, OG1 |
| Thr | CA, C, O | CA, CB, OG1 |
| Thr | CA, C, O | CB, CG2, OG1 |
| Asp | N, CA, C | CA, CB, OD2 |
| Asp | N, CA, C | CB, OD1, OD2 |
| Asp | CA, C, O | CA, CB, OD2 |
| Asp | CA, C, O | CB, OD1, OD2 |
| Glu | N, CA, C | CA, CB, OE2 |
| Glu | N, CA, C | CB, OE1, OE2 |
| Glu | CA, C, O | CA, CB, OE2 |
| Glu | CA, C, O | CB, OE1, OE2 |
| Asn | N, CA, C | CA, CB, ND2 |
| Asn | N, CA, C | CB, OD1, ND2 |
| Asn | CA, C, O | CA, CB, ND2 |
| Asn | CA, C, O | CB, OD1, ND2 |
| Gln | N, CA, C | CA, CB, NE2 |
| Gln | N, CA, C | CB, OE1, NE2 |
| Gln | CA, C, O | CA, CB, NE2 |
| Gln | CA, C, O | CB, OE1, NE2 |
| His | N, CA, C | CA, CB, NE2 |
| His | N, CA, C | CB, ND1, NE2 |
| His | CA, C, O | CA, CB, NE2 |
| His | CA, C, O | CB, ND1, NE2 |
| Lys | N, CA, C | CA, CB, NZ |
| Lys | N, CA, C | CB, CD, NZ |
| Lys | CA, C, O | CA, CB, NZ |
| Lys | CA, C, O | CB, CD, NZ |
| Arg | N, CA, C | CA, CG, NH2 |
| Arg | N, CA, C | CG, NH1, NH2 |
| Arg | CA, C, O | CA, CG, NH2 |
| Arg | CA, C, O | CG, NH1, NH2 |
| Cys | N, CA, C | CA, CB, SG |
| Cys | N, CA, C | N, SG, C |
| Cys | CA, C, O | CA, CB, SG |
| Cys | CA, C, O | N, SG, C |
| Met | N, CA, C | CA, CB, CE |
| Met | N, CA, C | CB, SD, CE |

TABLE 1-continued

| Amino Acid | Plane 1 | Plane 2 |
|---|---|---|
| Met | CA, C, O | CA, CB, CE |
| Met | CA, C, O | CB, SD, CE |
| Phe | N, CA, C | CA, CB, CE2 |
| Phe | N, CA, C | CB, CE1, CE2 |
| Phe | CA, C, O | CA, CB, CE2 |
| Phe | CA, C, O | CB, CE1, CE2 |
| Tyr | N, CA, C | CA, CB, OH |
| Tyr | N, CA, C | CB, CE1, OH |
| Tyr | CA, C, O | CA, CB, OH |
| Tyr | CA, C, O | CB, CE1, OH |
| Trp | N, CA, C | CA, CB, CZ3 |
| Trp | N, CA, C | CB, NE1, CZ3 |
| Trp | CA, C, O | CA, CB, CZ3 |
| Trp | CA, C, O | CB, NE1, CZ3 |
| Pro | N, CA, C | CA, CB, CD |
| Pro | N, CA, C | CB, CG, CD |
| Pro | CA, C, O | CA, CB, CD |
| Pro | CA, C, O | CB, CG, CD |

As can be seen from Table 1, a first plane might comprise only backbone atoms, for example. A second plane might comprise, for example, a combination of atoms chosen from the backbone and sidechain or atoms chosen only from the sidechain. The sidechain or terminal atoms may be unique.

A plane can also be defined by fitting to a set of atoms, which for example can be the six carbon atoms of aromatic ring systems. Any combination and number of atoms, larger or equal to three, can be used to define and fit a plane. Atoms can be part of the same or different residues.

The methods of defining plane angles herein can find use in a number of other applications as can be appreciated by those of skill in the art.

As can been seen from Table 2, sets of plane angle metrics can be defined for nucleic acids, such that they capture the alternate conformations of nucleotides.

TABLE 2

| nucleotide | Plane 1 | Plane 2 |
|---|---|---|
| G | O3', P, O5' | N1, C2, N2, N3, C4, C5, C6, O6, N7, C8 |
| G | O3', C3', C2' | N1, C2, N2, N3, C4, C5, C6, O6, N7, C8 |
| G | C2', C3', C4' | N1, C2, N2, N3, C4, C5, C6, O6, N7, C8 |
| G | O3', C3', C2' | N6, C4, C3' |
| G | C2', C3', C4' | N6, C4, C3' |
| C | O3', P, O5' | N1, C2, O2, N3, C4, N4, C5, C6 |
| C | O3', C3', C2' | N1, C2, O2, N3, C4, N4, C5, C6 |
| C | C2', C3', C4' | N1, C2, O2, N3, C4, N4, C5, C6 |
| C | O3', C3', C2' | N4, C5, C3' |
| C | C2', C3', C4' | N4, C5, C3' |
| A | O3', P, O5' | N1, C2, N3, C4, C5, C6, N6, N7, C8 |
| A | O3', C3', C2' | N1, C2, N3, C4, C5, C6, N6, N7, C8 |
| A | C2', C3', C4' | N1, C2, N3, C4, C5, C6, N6, N7, C8 |
| A | O3', C3', C2' | N6, C4, C3' |
| A | C2', C3', C4' | N6, C4, C3' |
| T | O3', P, O5' | N1, C2, O2, N3, C4, N4, O4, C5, C6, C7 |
| T | O3', C3', C2' | N1, C2, O2, N3, C4, N4, O4, C5, C6, C7 |
| T | C2', C3', C4' | N1, C2, O2, N3, C4, N4, O4, C5, C6, C7 |
| T | O3', C3', C2' | O4, C7, C3' |
| T | C2', C3', C4' | O4, C7, C3' |
| U | O3', P, O5' | N1, C2, O2, N3, C4, N4, O4, C5, C6 |
| U | O3', C3', C2' | N1, C2, O2, N3, C4, N4, O4, C5, C6 |
| U | C2', C3', C4' | N1, C2, O2, N3, C4, N4, O4, C5, C6 |
| U | O3', C3', C2' | O4, C5, C3' |
| U | C2', C3', C4' | O4, C5, C3' |

As can been seen from the example of beta-D-mannose in Table 3, sets of plane angle metrics can be defined for carbohydrates, such that they capture the observed conformations within polysaccharides.

TABLE 3

| Carbohydrate | Plane 1 | Plane 2 |
|---|---|---|
| BMA | C1, C2, O2 | C5, C4, C3 |
| BMA | C2, C1, O5 | C5, C4, C3 |
| BMA | C1, C2, O2 | O4, C4, C2 |
| BMA | C2, C1, O5 | O4, C4, C2 |
| BMA | C1, C2, O2 | O6, C6, C5 |
| BMA | C2, C1, O5 | O6, C6, C5 |

The set of residue metrics that will be calculated can include plane angles as described above, as well as backbone dihedral angles $\Phi$ and $\Psi$, sidechain dihedral angles $\chi_n$, where n is chosen according to, say, the type of amino acid, and distance vectors r between two points of the polypeptide. For example, r can be the vector pointing from $C^\alpha$ of a residue to a terminal atom of that residue.

Residue metrics $X^n_{ij}$ (where n refers to the metric, i refers to the residue number and j refers to the trajectory snapshot/frame or other conformational sample) are then calculated and stored in a database. Either all of the metrics defined for a residue, or a subset within, are used to identify the highly populated residue conformational sub-states sampled by the residue throughout the trajectory. The following description is based on the assumption that molecular dynamics is used as a sampling method, however data can be obtained by different means as described before, and processed according to methods of the invention.

Depending on the local environment of a residue, the residue may exist in more than one conformational state. For example, when a three-dimensional plot is used to plot the 3 angle metrics for a single residue, as shown in FIG. 2, two distinct clusters appear. These two clusters can be defined as alternate residue conformations for that residue as there are two separable populations. Multi-dimensional clustering is used to identify any highly populated separable residue conformations that occur throughout the trajectory. A multi-dimensional clustering method can be applied to this data.

For each residue independently, if the clustering algorithm identifies highly populated clusters, then these clusters are assigned a nominal descriptor from 0, 1, . . . , m. Trajectory frames wherein the residues belong to one of these highly populated clusters are assigned the appropriate cluster descriptor. Specifically, the time trajectory data for a residue metric or residue is assigned this descriptor based on its cluster membership $X^{mn}_{ij}$. Some of the trajectory data points will not belong to a significantly populated cluster; these are labeled with a nominal descriptor of −1 indicating that property.

Multiple residue metrics can be combined in such a way that they uniquely define all of the resolvable alternate residue conformations in the data (for example, if all of the standard plane angles and/or dihedral angles are used). In those use cases, the residue descriptor defines a unique residue conformation.

Figure 3:
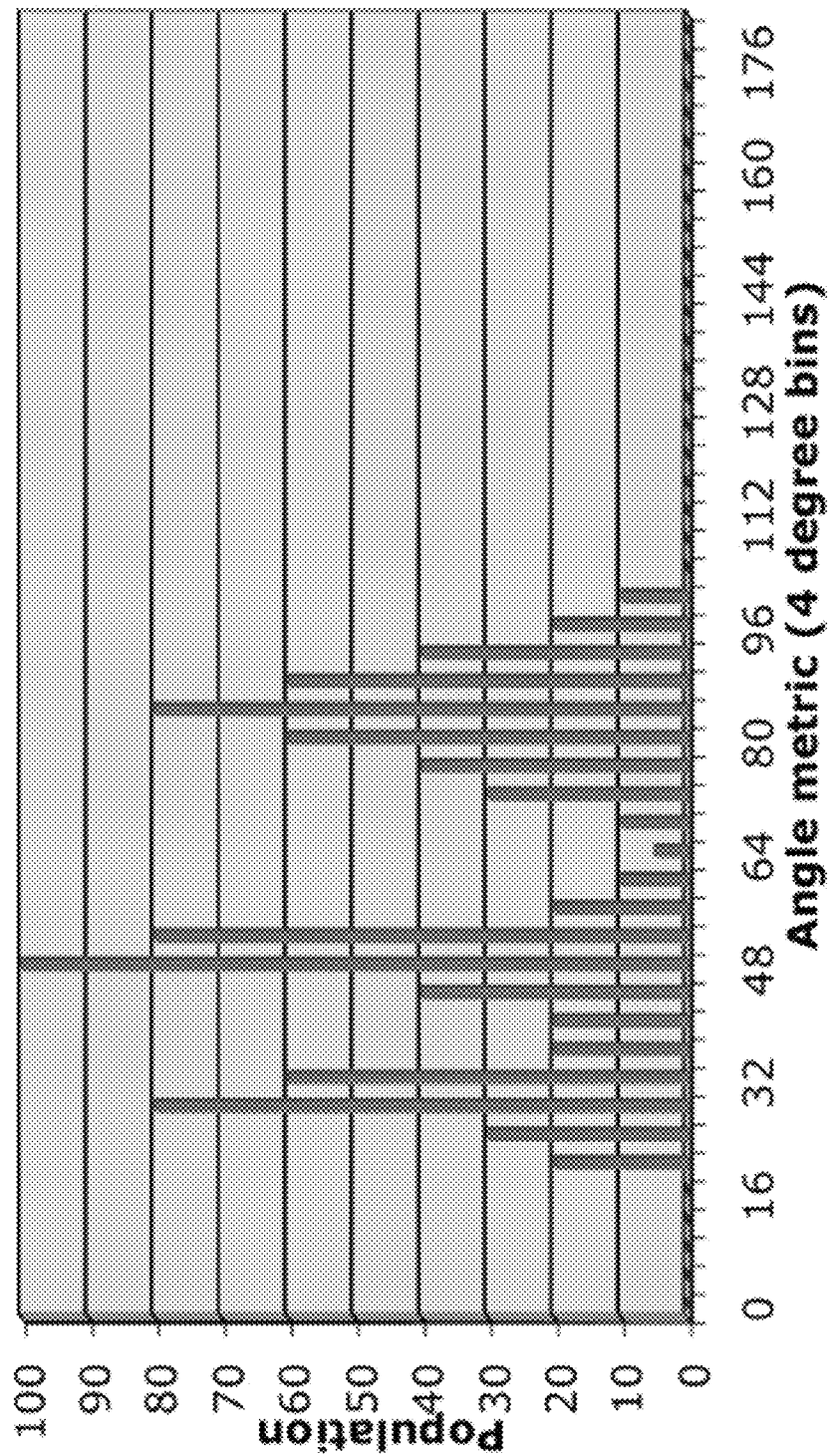
FIG. 3 shows a histogram of geometric metric data derived from a molecular dynamics simulation. The peaks and valleys of the histogram suggest a multimodal distribution having three local maxima.
Figure 4A:
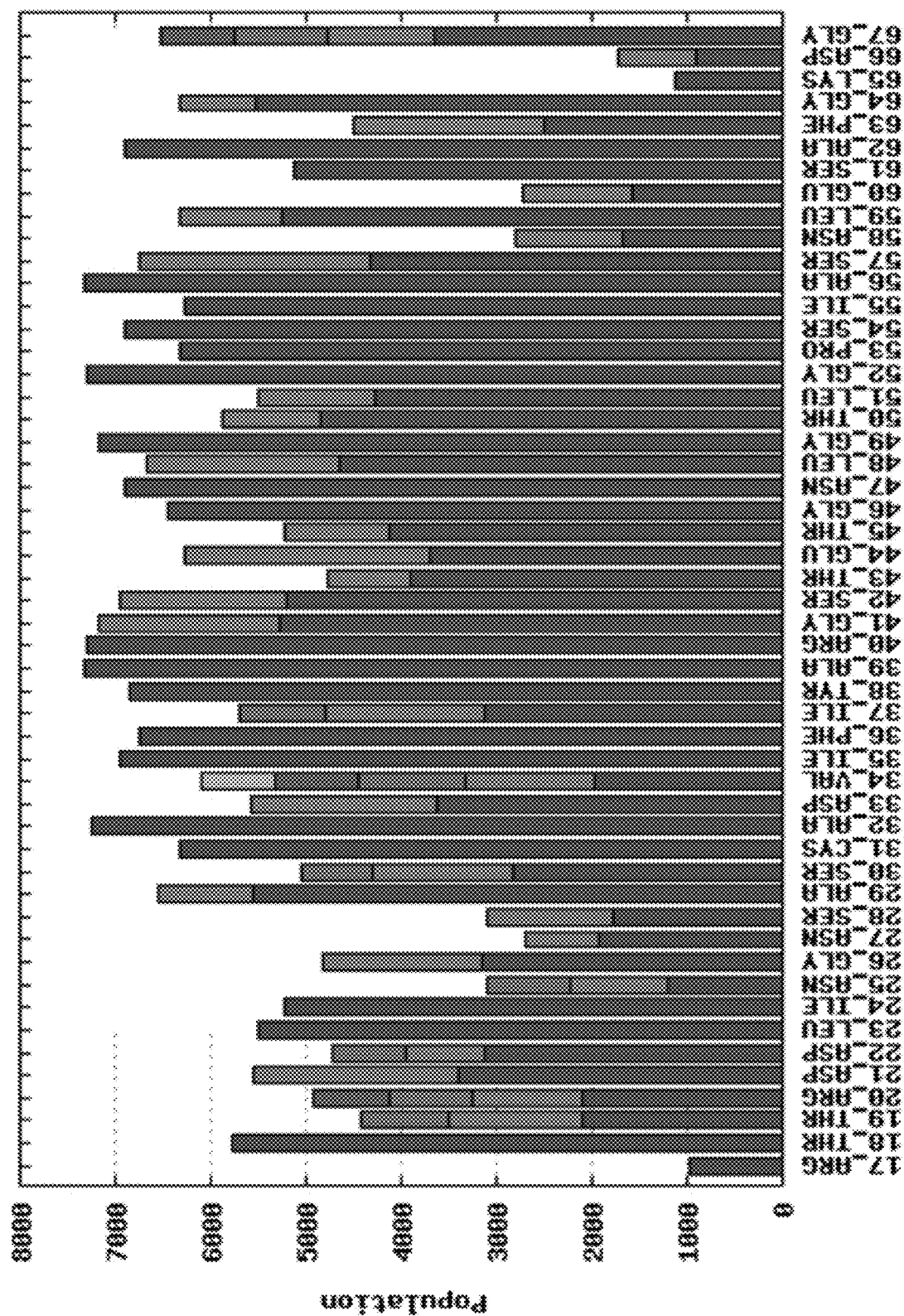
FIG. 4A-FIG. 4E shows column-stacked histogram plots of the residue conformations that the method defines for cutinase. These plots display the unique signature of the protein and are used to quickly visualize residues that have single residue conformations, those that have alternate conformations and those residues that have highly populated discrete conformations. Specific details are provided in the examples section.
Figure 4B:
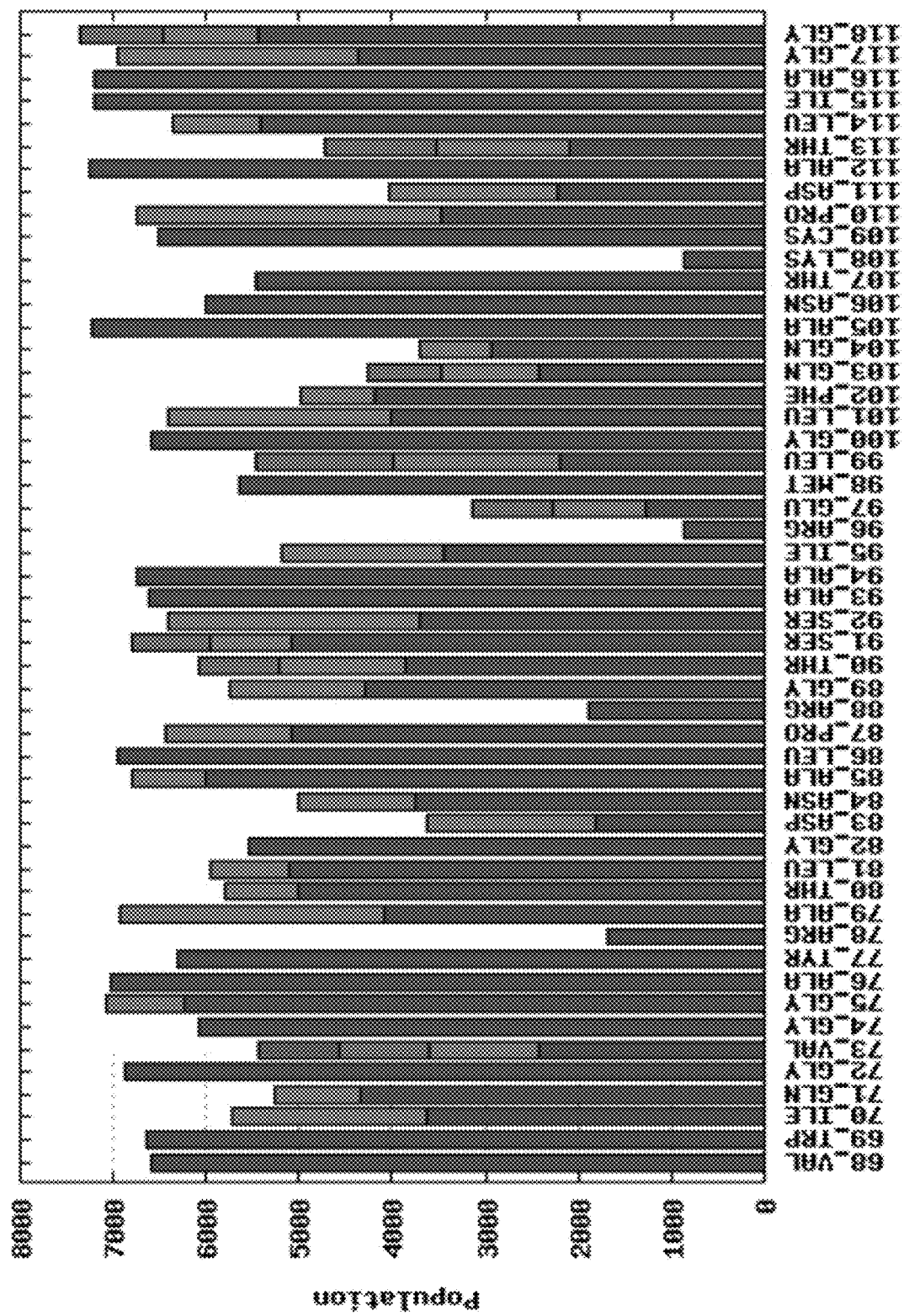
Figure 4C:
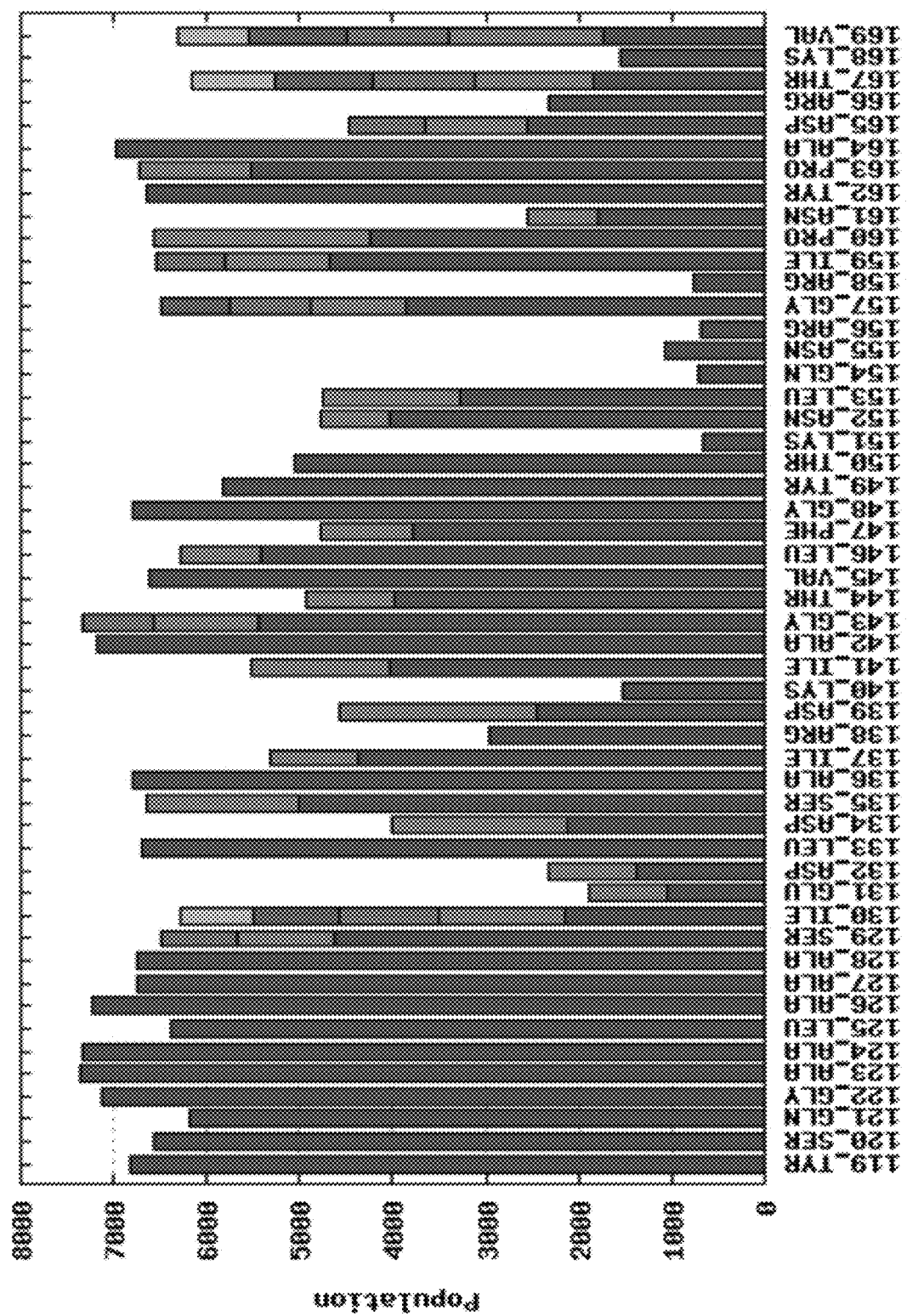
Figure 4D:
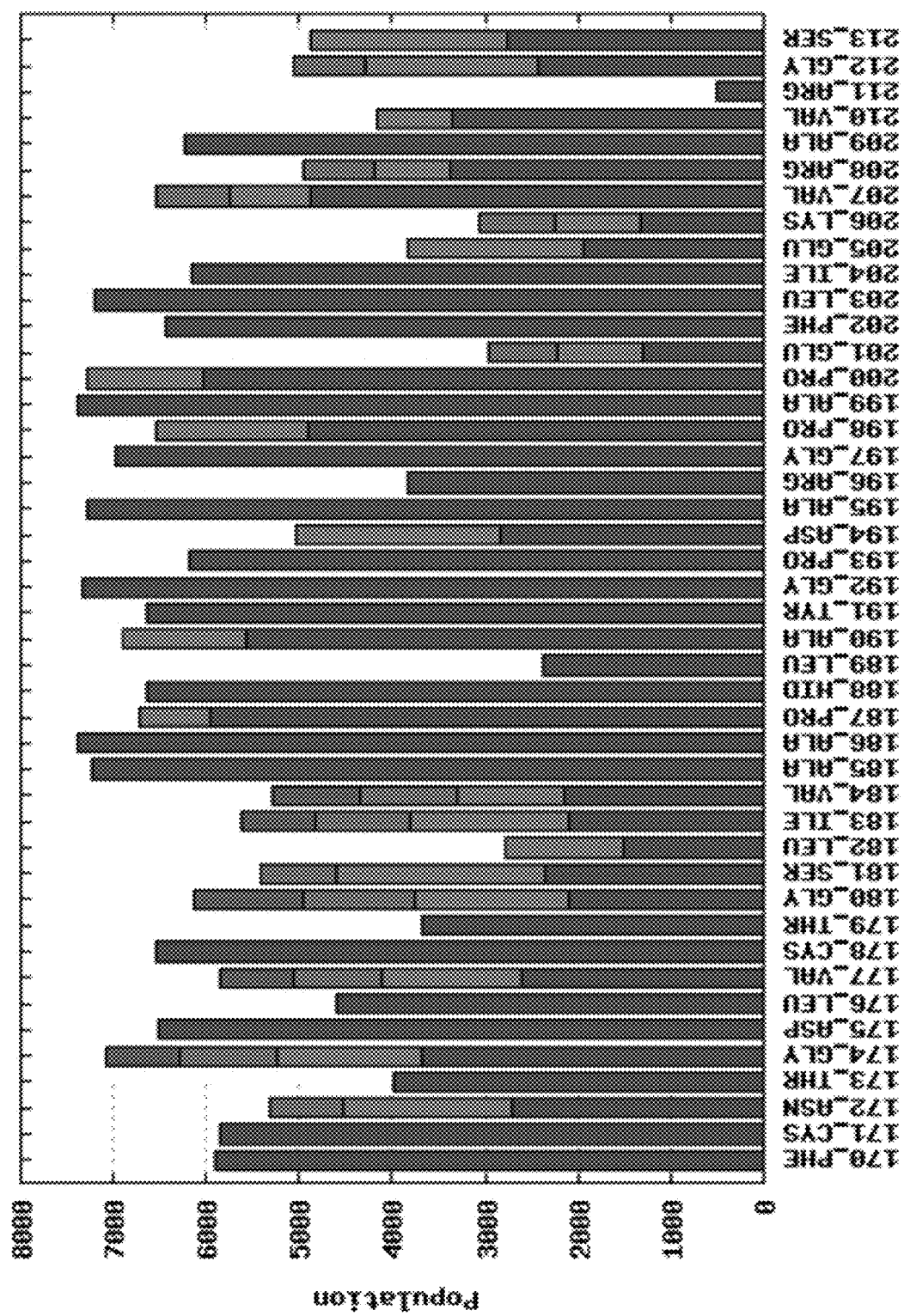
Figure 4E:
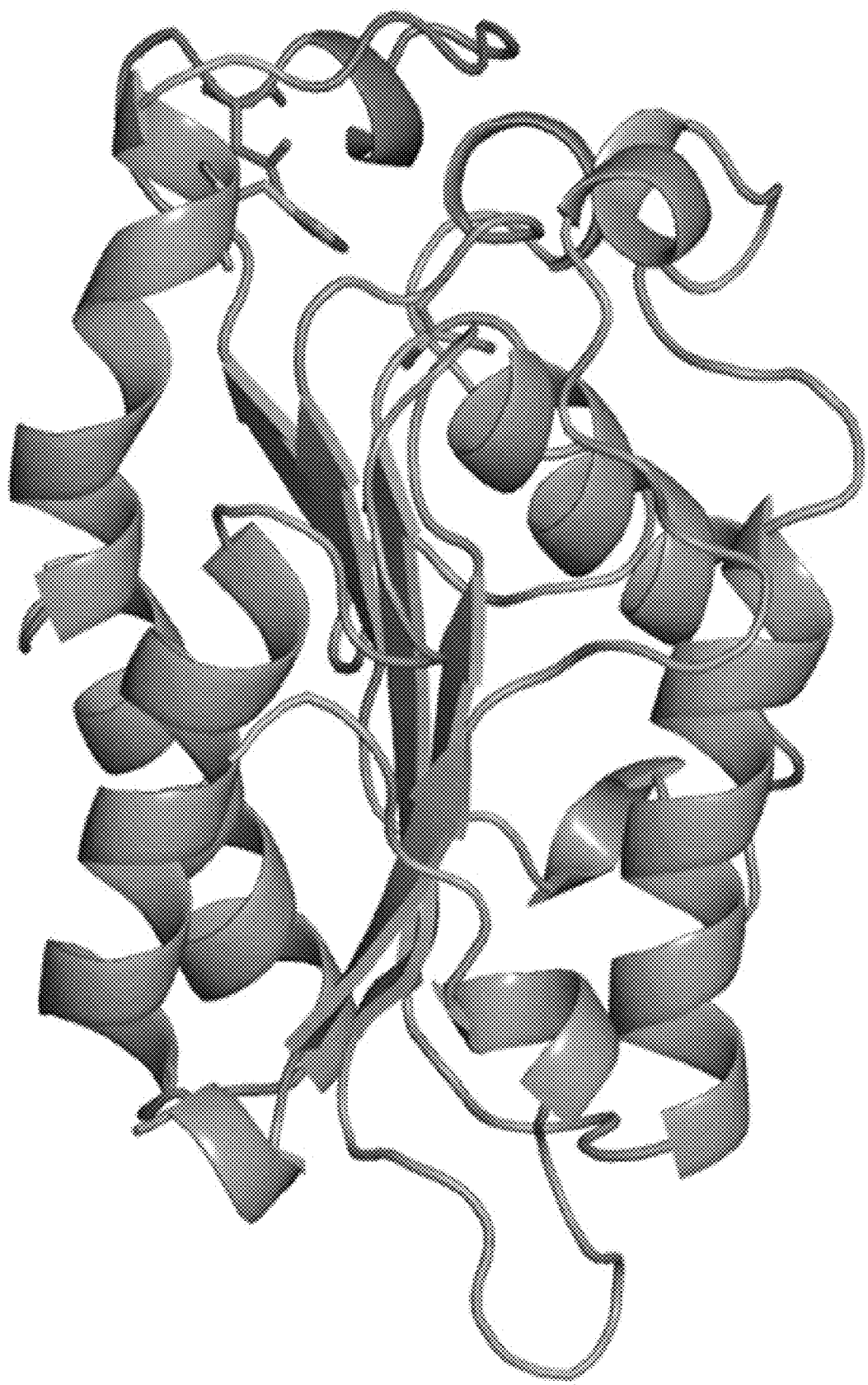

A single residue metric trajectory, $X^n_{ij}$ can be used to characterize structural sub-states of the residue. Herein we describe a binning method as opposed to any standard clustering method, to characterize single metric data that inherently shows more positional overlap but still contains peak differentiation. The values of the residue metric are binned together according to a chosen bin width that is appropriate for the metric type. For example, in the analysis of a dihedral angle metric, a chosen bin width of 4° would give sufficient resolution to separate conformers that differ by 10° while at the same time provide sufficient smoothing to limit statistical noise. As shown in FIG. 2, three clusters are distributed about local maxima in which the angle metric are in "bins" 28-32, 48-52 and 84-88, however, depending on the criteria for assigning clusters, more or fewer clusters may be discerned. Other bin widths can be chosen to provide the desired smoothing and resolution. Automated single- and multi-dimensional binning programs may be useful in determining bins. Populations of the bins are then determined and plotted to yield a histogram showing the distribution of residue metric, an example of which is shown in FIG. 3.

These smoothed histograms can be then be used to define the most probable residue metrics. The boundaries between the peaks in the histogram (see FIG. 3) are used to define the structural confines of a resolvable residue metric minimum, as the peaks result from observed significant data point frequencies at a particular angle or distance.

The trajectory data can then be assigned a nominal descriptor based on the metrics occupation in one of these defined populated bins. As used herein, a residue "sub-state" refers to a delineated set of values. Sub-states X can then be identified by applying a set of criteria to the population distribution of the residue metric. These clusters serve to identify the probable residue conformation states of the residue metrics for cluster X. For example, the histogram in FIG. 3 shows three clusters that can be identified according to the peaks and valleys of the distribution, FIG. 2 shows two clusters identified by separating three dihedral angles, without previous binning of the data. The number of clusters in a given distribution will vary according to the different thresholds and constraints that one of skill in the art applies in processing and interpreting the data. For example, narrowing or widening the bin width will change the population profile accordingly, and hence the number of peaks and valleys will change. The step of identifying clusters can be automated. Bravi et al., 1997, *Journal of Computational Chemistry*, 18, 1295, describe an example of automated quantitative method for identifying clusters.

As used herein, "alternate" as in "alternate clusters" or "alternate conformational states," for example, means highly populated but not necessarily the most populated. Criteria for determining what counts as highly populated are discussed herein.

(Residue Profiling)

A residue profile is the summary of analysis performed on a per residue basis as described in more detail in the following paragraphs. The mobility index is derived from cluster frequency and variance in the geometric data used for clustering.

It is noted that the nominal descriptor, assigned by either a clustering or the alternative binning method, defines a conformational sub-state of the residue. Both the occurrence/population and number of conformational states sampled by a residue during the course of the trajectory can be analyzed using standard graphical display methods such as pie charts and histograms. This information allows a skilled worker to draw conclusions on the structure and functional importance of the respective residues.

Residue conformations can be identical to conformations described in rotamer libraries (Dunbrack) but can also be of off-rotamer conformations as described supra. Alternate residue conformations are identified by grouping/clustering similar conformations together with parameters defined by the respective clustering algorithms. No hard cutoff values are used to define clusters of configurations, thus, for example a conformation can span a wide angle for one of the measured dihedral angle with a large standard deviation, if the distribution is continuous along that angle.

These residue conformations (or sub-states) help to define the motional characteristics of a residue. They can be used to identify, for example, structural mobility and/or directionality in the movements of a residue. For example, the angular variance of these defined sub-states can be used, in an analogous fashion by those skilled in the art, to derive functional information similar to what is obtained by close examination of the anisotropic atomic temperature factors for atoms in sub-atomic resolution crystal structures. This data in a qualitative fashion defines the potential energy landscape defining the residue's positional freedom to move and alter its structural conformation.

Analyzing the features of a distribution, one can distinguish between mobile and rigid residue metrics. Mobile residue metrics are characterized by broad, featureless distributions. Rigid or nearly rigid residue metrics are characterized by relatively narrow peaks with a clustering of the population around a certain value of the residue metric. A distribution is considered to be broad and featureless if it lacks at least one narrow peak.

Residues can be grouped into rigid, semi-rigid, flexible and mobile groups based on the properties of their respective defined alternate conformation(s). The designation into a 'mobility group' can be done based on a series of measurements and cutoff values. This classification and the corresponding cutoff values can be adjusted to best fit the analyzed system. Classification of residues is done based on population of different conformations and the respective variance within these conformations.

From the above residue profiles, protein profiles can be derived and can be used for comparison with other proteins, or mutated forms of the same protein. This information can be used by a person skilled in the art to direct protein engineering efforts.

In a preferred embodiment, all residues defined as very rigid using the residue profile method can be assigned to a framework, which by definition is crucial for the integrity of the protein structure and thus has to be treated with special care when attempting to mutate the protein. This framework could be considered as a special case of a residue network.

(Residue Networks)

A residue network is described as a set of residues that show high interrelatedness based on statistical analysis of residue conformations, as described in more detail below.

As discussed above, the nominal residue conformational descriptor can either be assigned based on single residue metric or on a subset or all residue metrics defined for that residue, depending on the number of metrics used in the clustering/binning process. Multi-dimensional clustering with a subset of residue metrics that sample all the structural degrees of freedom for a residue, essentially defines all of the resolvable residue conformations or sub-states or "alternate-conformations" available for a particular residue sampled within the trajectory data.

Most residues in a protein are typically quite immobile and upon analyzing their associated metrics, only a few alternate conformations result. After defining these alternate residue conformations (sub-states) for each residue, the population of each defined residue conformation sub-state throughout the trajectory can be calculated.

The marginal probability of a residue conformation can be calculated as the quotient of the residue conformation population divided by the total number of frames. For example, for a residue conformation "A":

$$P(A)=n(A)/N$$

Where P(A) is the marginal probability, n(A) is the population of A and N is the total number of frames.

An alternate conformation is considered to be a unique residue conformational substrate and a probability can be assigned to it if the subset satisfies the central limit theorem and the distribution has converged. Cases in which the probability of state A for a residue P(A) is equal to (or close to) 1 is considered to be rigid and part of the framework described above.

These residue conformation populations are then further analyzed to determine correlations between the clusters.

For two residues in conformational states A and B, respectively, where P(A) and P(B) are not equal to 1, i.e. the residues are not part of the framework, conditional probabilities are calculated for each pair of conformation using the formula:

$$P(A|B)=P(A,B)/P(B)$$

Where P(A|B) is the conditional probability for A given B, P(A,B) is the intersection of A and B (or joint probability) and P(B) the marginal probability for B.

A normalization of this probability ratio is carried out in the form P(A|B)/P(A) i.e. P(A,B)/P(A)P(B). This normalized probability ratio is used to verify the extent of statistical independence or a measure of dependence and correlation between the two residue conformational states A and B. A value of 1 for this ratio suggests that A and B are statistically independent. Likewise a deviation from one implies that A and B are correlated.

An "energy" like term can be described by taking the natural logarithm as:

$$G=-\ln(P(A|B)/P(A))$$

A value of 0 for this free energy estimate suggest the two conformations are statistically independent. Positive values of E indicates the mutual exclusion of two conformations, while negative values infer coexistence.

In summary, in the case of an uncorrelated metric pair, the log of the ratio will tend towards zero whereas correlated residues will produce ratios that significantly deviate from zero. The underlying cause of the time-correlations between the metrics may be quite complex and can result from either direct or indirect interactions of the respective protein residues.

Alternatively, the difference between the marginal and the conditional probability can be used to describe the amount of correlation between two residue conformations.

In practice, various statistical methods deriving statistical significance between populations can be applied to identify correlated residue conformations. One example of such a method would be the use of contingency tables.

A reduced subset of correlated residue conformation pairs can be created by applying cutoffs based on the histogram distribution of the probability ratio values for all of the residue conformation pairs. For example, the random error in the data is evident by the bulk distribution of the ratio data as the majority of the data is not significantly correlated and thus has a ratio near or at unity. A cutoff that removes this bulk of the data leaves only those correlated residue pairs whose ratio is significantly different than the general background variation due to weak correlations or the random noise in the populations of residue conformations.

Residue conformations that are significantly correlated may either co-exist or may be mutually exclusive throughout the trajectory. Both types of correlations are critical to define the residue interaction networks that exist within proteins. For example, steric interactions between residues are predominately identified as mutually exclusive interactions. Co-existence or mutual exclusion are evident in the sign of G, residue pairs with a negative correlation value have an increased propensity to exist together, whereas positive values of G suggest mutual exclusion.

Residue interaction networks can be defined by the interdependence of the strongly correlated pair wise residue-residue interactions. For example, when the position of one conformational state of a residue, A, influences the populations of the second residue's conformation B and a third residue conformation C, then all three residues can be identified as belonging to a network.

In many cases, the position of one conformational state A will not influence the populations of residue conformation B in a drastic fashion. That is, there will be changes in the propensity for a residue, $Y_j$ to be in residue conformation B when residue $X_i$ is in position A. This is an indirect measure of the change in the potential energy landscape. These less obvious residue-residue correlation pairs are also potentially involved in a correlated residue network.

Residues that are involved in a correlated residue network by definition require high pair wise interconnectivity between their respective residue conformations. For example, for the network of 4 residue conformations, A, B, C and D, one will expect that there are more than 3 pair wise correlations defining that network if it is a "correlated residue network". Ideally, one would expect to observe 6 pair wise correlations for a correlated network involving the 4 residue conformations. In summary, highly interconnected residue conformations in a network define a correlated residue network.

Various filtering methods can be used to elucidate the likely mechanism(s) responsible for the observed correlated residue network. For example, distance constraints can be used to identify through space interaction networks. If two residue conformations (or residues) A and B, are within van der Waals distance (e.g. within 4.5 Angstroms) at any time throughout the trajectory then they are positioned such that they physically contact each other.

The residue metric cluster information ($X_{ij}^{mn}$) can be used in a time series analysis. A time series of residue metrics in the course of the simulated trajectories is derived on the basis of assignment to these unique clusters. Time dependent covariance analysis of the residue geometry metrics, with methods performed according to the art, will provide information on coupled residue geometry changes in the system as a function of time.

Data mining approaches including Principal Component Analysis (PCA) or Correspondence Analysis can be employed to analyze the covariance matrix.

The geometrical covariance data in time domain can be transformed to frequency domain to apply traditional signal processing procedures in analysis of the data.

In another embodiment of the invention the correlations are not calculated for pairs of conformations but for residue-residue pairs by calculating the mutual information I(A;B) with the formula:

$$I(A;B)=\Sigma_A\Sigma_B P(A,B)*\log(P(A,B)/P(A)*P(B))$$

Where P(A,B) is the conditional probability of A given B and P(A) and P(B) are the marginal probabilities for A and B respectively, summed over all the relevant correlated conformational sub-states of the residues A and B. Other methods such as the Z-score computation (also known as the observed minus expected squared (OMES) covariance algorithm) can be applied to analyze this relation between pairs of residues.

Applications

The "protein profile" data from a protein can be used to differentiate proteins and thus classify proteins into different groups. Such a new classification scheme does not rely on currently used parameters such as structure and sequence similarity but uses the relative number of residues conformations and their respective flexibility to differentiate between proteins. Such groups can for example be used to describe the overall flexibility of a protein and correlated to physical properties such as stability.

For every protein, a set of residues will have very little flexibility; these residues constitute a framework for the respective structure. The information about which residue belongs to a framework can be a used to either avoid mutations, if the integrity of that frameworks should not be disturbed, or in case disruptions to this integrity are wanted can be specifically targeted by mutations. Protein profiles can be used to estimate of how amenable a protein in general is to mutations, and help a person skilled in the art to identify positions that tolerate mutations.

Clustering of residues with small positional variance in their defined residue conformation(s), can be used as an additional method to identify key binding sites in the protein. These sites are often referred to as "hot spots" by those skilled in the art.

Residues with larger positional variance in their defined residue conformation(s) can be selected for targeted mutagenesis applications aimed at improving protein stability. Protein stability is often associated with compactness of the protein. (Matthews, B., 1996, FASEB J., 10(1), 35; Stawiski, E. W., et. al., 2000, PNAS, 97(8), 3954)

The observed residue conformations defined by this method can be used to develop a weighting scheme to prioritize a restricted set of residue types, using dead-end elimination like methods for the design of variants (Desmet et al., 1992, Nature, 356, 539). Since it will be energetically less favorable for some residue types to be substituted at a position where the backbone geometry requirements are not consistent with the residue's rotameric conformations, by defining the dynamic range of the more probable conformational space one can screen the known rotamer library to identify and weight for alternative residue types.

Correlations between two residues can, without further analysis of the networks that they are involved in, be used to design cooperative mutations. Two residues, when they are located next to each other and thus have van der Waals contacts, or, when they are located at a distance through electrostatic interactions, can influence each others position and it is thus necessary to consider the effect on all the correlated neighbors. Strongly correlated residues could be considered for simultaneous mutagenesis.

Determination of correlated networks of residues within a protein can be useful for predicting protein flexibility, which plays an important role in ligand binding. Processes such as enzyme catalysis often involve the preferential binding of the transition-state of the molecule undergoing a reaction. The ability of an enzyme to catalyze a reaction is linked to its ability to stabilize a transition-state. In terms of a free energy function, the enzyme is thought to lower the energetic barrier that must be overcome by reactants before reaching the product state along a reaction coordinate.

More generally, understanding networks of correlated motion within a molecule can allow a researcher to fine tune the ability of two binding partners to interact or bind to each other, especially when one of those binding partners is a protein. Thus, establishing correlated motions between the parts of binding partners may have important implications in controlling signaling events or any other biological process in which binding is important.

In one aspect, the present invention may be useful in protein docking methods, which are computational procedures used in determining the structure of complexes between a protein and another molecule, such as another protein or a ligand. In early methods, bond angles, bond lengths and torsion angles of the various protein residues were kept fixed during simulation. Eventually, flexible docking methods were developed that allowed for conformational changes, particularly of the sidechains, during simulation. The characterization and identification of correlated residue networks through the methods of the present invention allow for the definition of key flexible subsets of residues to include in such flexible docking methods. One advantage of the present methods is that they allow one to identify and include in a protein docking simulation a number of residues outside the first "shell" of the protein active site. Thus, the inclusion of distant residues whose movement is involved in binding interactions can be used to improve current docking methods.

Characterization of the probable residue conformations in an active site can also be used to provide a limited set of protein conformations for rigid body docking methods, thereby substantially reducing the combinatorial explosion property when creating rigid protein models.

An understanding of how protein residues, and their respective conformation(s), are correlated enable one to engineer either enzyme catalysts or substrates for improved or reduced catalytic efficiency compared to previously known binding pairs. Knowledge of residue correlations can also aid in the engineering of novel binding partners with different specificity compared to a previously known binding partner.

Thus, in another aspect, the invention provides for the engineering of a ligand for a protein. By determining correlations between protein residues and using spatial or distance constraints to map networks of the correlated residues, one will be able to characterize conformational states of the protein. New binding sites can be determined such that a protein function, such as enzymatic catalysis, protein-protein or protein-substrate binding, may be modified upon ligand binding to the new binding site. Thus, the present invention can be used to identify potential allosteric sites. The networks can be used to design or modify ligands to optimize binding, enantioselectivity or substrate specificity.

The identified protein conformational states can also be used to engineer the flexible architecture that may be required to maintain binding or activity for an enzyme. Thus, the present methods can be useful for identifying the inherent flexibility requirements for the ligand. This can be especially important for the design of antibiotics.

In another aspect, the present invention finds use in molecular dynamics/quantum mechanics simulations to characterize the optimal spherical boundary conditions by identifying distant regions of the protein that contribute significantly to the geometry at the active site.

In one aspect, the present invention provides methods of designing protein variants that have altered functional characteristics compared to wild-type protein or other variants of a protein. A "protein variant" means a protein that differs from a wild-type protein by at least one residue. The difference between a protein variant and the wild-type protein can be due to addition, deletion or substitution of an amino acid at any chosen mutational position. The wild-type protein may be a naturally occurring polypeptide or a variant or engineered version of a naturally occurring polypeptide. Parent polypeptide may refer to the wild-type protein or variants or compositions that comprise the parent polypeptide.

Correlating residues and determining networks of correlated residues clarifies which residues and their motions are most important for ligand binding. Modifying these residues may be used to alter enantioselectivity, substrate specificity, enzyme activity and mechanism, and product profiles. Modification of polypeptide function can cause altered polypeptide stability. Thus, the present invention also provides for methods of altering polypeptide stability. In one embodiment, the thermal stability or pH stability is altered by modifying the sequence of a polypeptide. In one embodiment, identification of allosteric networks can allow for the design of protein variants that can interact with a ligand of choice.

Once designed, proteins may be easily manufactured by known methods. For example, methods of protein expression using exogenous nucleic acid into host cells are well known in the art and will vary with the host cell used. Techniques of exogenous nucleic acid introduction include but are not limited to dextran-mediated transfection, calcium phosphate precipitation, calcium chloride treatment, polybrene mediated transfection, protoplast fusion, electroporation, viral or phage infection, encapsulation of the polynucleotide(s) in liposomes, and direct microinjection of the DNA into nuclei. In the case of mammalian cells, transfection may be either transient or stable.

In one embodiment, proteins are purified or isolated after expression. Proteins may be isolated or purified in a variety of ways known to those skilled in the art. Standard purification methods include chromatographic techniques, including ion exchange, hydrophobic interaction, affinity, sizing or gel filtration, and reversed-phase, carried out at atmospheric pressure or at high pressure using systems such as FPLC and HPLC. Purification methods also include electrophoretic, immunological, precipitation, dialysis, and chromatofocusing techniques. Ultrafiltration and diafiltration techniques, in conjunction with protein concentrating methods, are also useful. For general guidance in suitable purification techniques, see *Protein Purification: Principles and Practice* (3rd ed., 1994).

In one embodiment, the functional and/or biophysical properties of the molecules of the present invention are screened in an in vitro assay. In vitro assays may allow a broad dynamic range for screening properties of interest. Properties of the molecule that may be screened include but are not limited to stability and solubility. In addition, polypeptides may be screened in vitro for affinity for ligands, enzymatic activity, or biological activity. Multiple properties may be screened simultaneously or individually. The molecules may be purified or unpurified, depending on the requirements of the assay. Binding assays can be carried out using a variety of methods known in the art, including but not limited to FRET (Fluorescence Resonance Energy Transfer) and BRET (Bioluminescence Resonance Energy Transfer)-based assays, AlphaScreen™ (Amplified Luminescent Proximity Homogeneous Assay), Scintillation Proximity Assay, ELISA (Enzyme-Linked Immunosorbent Assay), SPR (Surface Plasmon Resonance, also known as BIACORE®), isothermal titration calorimetry, differential scanning calorimetry, gel electrophoresis, and chromatography including gel filtration. Assays may employ a variety of detection methods including but not limited to chromogenic, fluorescent, luminescent, or isotopic labels.

Protein stability may be determined by measuring the thermodynamic equilibrium between folded and unfolded states. For example, polypeptides designed and subsequently engineered using the present invention may be unfolded using chemical denaturant, heat, or pH, and this transition may be monitored using methods including but not limited to circular dichroism spectroscopy, fluorescence spectroscopy, absorbance spectroscopy, NMR spectroscopy, calorimetry, and proteolysis. As will be appreciated by those skilled in the art, the kinetic parameters of the folding and unfolding transitions of a polypeptide may also be monitored using these and other techniques. The solubility and overall structural integrity of a molecule may be quantitatively or qualitatively determined using a wide range of methods that are known in the art. Methods which may find use in the present invention for characterizing biophysical properties include gel electrophoresis, chromatography such as size exclusion chromatography and reversed-phase high performance liquid chromatography, mass spectrometry, ultraviolet absorbance spectroscopy, fluorescence spectroscopy, circular dichroism spectroscopy, isothermal titration calorimetry, differential scanning calorimetry, analytical ultra-centrifugation, dynamic light scattering, proteolysis, and cross-linking, turbidity measurement, filter retardation assays, immunological assays, fluorescent dye binding assays, protein-staining assays, microscopy, and detection of aggregates via ELISA or other binding assay. Structural analysis employing X-ray crystallographic techniques and NMR spectroscopy may also find use. In one embodiment, stability and/or solubility may be measured by determining the amount of a molecule in solution after some defined period of time, in normal conditions or extreme.

In a preferred embodiment, molecular activity is determined using cell-based or in vivo assays. For such assays, a molecule is typically added to growth medium to expose the cell to the molecule. The response of cells to the molecule, for example cell survival, cell death, change in cellular morphology, or transcriptional changes and their effect on expression of a natural gene or reporter gene. Methods for monitoring cell death or viability are well known in the art, and include the use of dyes, immunochemical, cytochemical, and radioactive reagents. Cell types for such assays may be prokaryotic or eukaryotic, and a variety of cell lines that are known in the art may be employed.

Alternatively, cell-based screens are performed using cells that have been transformed or transfected with nucleic acids encoding a polypeptide of the invention.

The biological properties of the molecules of the present invention may be characterized in cell, tissue, and whole organism experiments. As is known in the art, drugs are often tested in animals, including but not limited to mice, rats, rabbits, dogs, cats, pigs, and monkeys, in order to measure a drug's efficacy for treatment against a disease or disease model or to measure a drug's pharmacokinetics, toxicity, and other properties.

The methods described herein can thus be applied to or useful with any biopolymer or biomolecule of interest. In one embodiment, the biopolymer is a protein or polypeptide as defined above. Proteins of particular use include enzymes, antibodies (for example, antifluorescein), oxidases, hydrolases, lipases, aldolases and peptide analogs. In one embodiment, the oxidase is cholesterol oxidase. In one embodiment, the biopolymers are saccharides (including polysaccharides), nucleic acids, and nucleic acid-saccharide conjugates (for example, UDP-galactopyranose). In another embodiment, the biomolecules may also include therapeutic small molecules. In one embodiment, the biomolecules include complexes of, for example, the above molecules and other molecules described herein. Examples of complexes include antibody-saccharide, antibody-peptide, and antibody-peptide analog complexes. Any of these molecules may also be engineered.

The methods and processes described may be implemented as computer programs that are executed on programmable computers comprising at least one processor and at least one data storage system. A computer program is a set of instructions that can be used, directly or indirectly, in a computer to perform a certain activity or to bring about a certain result. A computer program can be written in any form of programming language, including compiled or interpreted languages, and it can be deployed in any form, including as a stand-alone program or as a module, component, subroutine, function, procedure or other unit suitable for use in a computing environment.

The computer program can be stored on a computer-readable storage medium or device. Examples of storage media include, without limitation, optical disks such as CD, DVD and Blu-ray Discs (BD); magneto-optical disks; magnetic media such as magnetic tape and internal hard disks and removable disks; semi-conductor memory devices such as EPROM, EEPROM and flash memory; and RAM. The processor and the memory can be supplemented by or incorporated in application-specific integrated circuits (ASICs). When read into the processor of the computer and executed or further processed before execution, the instructions of the program cause the programmable computer to carry out the various operations described above.

To provide for interaction with a user, the invention can be implemented on a computer having a display device such as, for example, a cathode ray tube (CRT) or liquid crystal display (LCD) monitor for displaying information to the user. The user can provide input, for example, via a keyboard and a pointing device such as a mouse. The residue correlations and networks data can be represented graphically using molecular modeling and graphics software.

The different aspects of the invention can be implemented in a computer system that includes a backend component such as a data server, a middleware component such as an application server or an Internet server, or a frontend component such as a client computer having a user interface, Internet browser or any combination thereof.

The components of the system can be connected by any form or medium of digital data communication.

Accordingly, in various embodiments, the invention provides a method of determining biopolymer profiles based on the dynamic behavior of individual component structural units comprising performing a simulation to calculate at least one trajectory for a plurality of geometric metrics, wherein the plurality of geometric metrics comprises a plane or dihedral angle metric or a distance metric; determining at least one conformational frequency for a cluster based on a subset of geometric metrics or the plurality of geometric metrics for each of the structural units; and assigning a mobility index to every structural unit, based on conformational frequencies and mobility.

In various embodiments, the invention provides a method of determining polypeptide profiles based on the dynamic behavior of individual residues comprising performing a simulation to calculate at least one trajectory for a plurality of residue metrics, wherein the plurality of residue metrics comprises a plane or dihedral angle metric or a distance metric; determining at least one conformational frequency for a cluster based on a subset of residue metrics or the plurality of residue metrics for each of the residues; and assigning a mobility index to every residue, based on conformational frequencies and mobility.

In various embodiments, the invention provides a method of determining correlations between residues of a polypeptide comprising performing a simulation to calculate at least one trajectory for a plurality of residue metrics, wherein the plurality of residue metrics comprises a plane or dihedral angle metric or a distance metric; determining at least one conformational frequency for a cluster based on a subset of residue metrics or the plurality of residue metrics for each of the residues; and correlating the conformational frequency of residue clusters, thereby determining correlations between residues of the polypeptide.

In various embodiments, the invention provides a method of determining correlations between residues of a polypeptide comprising performing a simulation to calculate at least one trajectory for a plurality of residue metrics, wherein the plurality of residue metrics comprises a plane or dihedral angle metric or a distance metric; determining at least one conformational frequency for a cluster based on a subset of residue metrics or the plurality of residue metrics for each of the residues; and correlating the conformational frequency of clusters, wherein at least one of the residue conformations corresponds to an off-rotamer conformation of a residue, thereby determining correlations between residues of the polypeptide.

In various embodiments, the invention provides a method according to any preceding paragraph wherein at least two of the residue conformations independently correspond to either a rotamer or off-rotamer conformation of the residue.

In various embodiments, the invention provides a method according to any preceding paragraph wherein at least one of the correlations, if determined, is between alternate conformational states of residues.

In various embodiments, the invention provides a method according to any preceding paragraph wherein the plurality of residue metrics comprises a residue metric selected from the group consisting of a dihedral angle, a position vector and a plane angle metric or a distance metric.

In various embodiments, the invention provides a method according to any preceding paragraph wherein the plane angle metric is calculated using a first and a second plane of a residue, the first plane defined by a first set of atoms comprising a backbone atom of the residue and the second plane defined by a second set of atoms comprising an atom selected from the group consisting of a backbone atom and a terminal atom of the residue.

In various embodiments, the invention provides a method according to any preceding paragraph wherein the first set of atoms is selected from the group consisting of ($C^{\alpha}$, $C^{o}$, N) and ($C^{\alpha}$, $C^{o}$, O).

In various embodiments, the invention provides a method according to any preceding paragraph wherein the determining step comprises using a multidimensional clustering method.

In various embodiments, the invention provides a method according to any preceding paragraph wherein the determining step comprises running an automated binning program.

In various embodiments, the invention provides a method according to any preceding paragraph wherein the correlating step, if present, comprises performing cluster frequency analysis.

In various embodiments, the invention provides a method according to any preceding paragraph wherein the cluster frequency analysis comprises calculating a frequency for a first conformation of a first residue using a plurality of trajectory frames; calculating a frequency for a second conformation of a second residue using a plurality of trajectory frames; calculating a frequency for the second conformation using a subset of the trajectory frames; and determining if conformational frequencies of the first conformation and the second conformation show statistical dependency.

In various embodiments, the invention provides a method according to any preceding paragraph further comprising filtering redundant data.

In various embodiments, the invention provides a method according to any preceding paragraph wherein the polypeptide is selected from the group consisting of structural protein, antibody, enzyme and signaling protein.

In various embodiments, the invention provides a method of determining a network of correlated residues of a polypeptide comprising determining polypeptide profiles or correlated residues of the polypeptide by performing the method according to any of the preceding paragraphs; and mapping the network of correlated residues by using a spatial or distance constraint, thereby determining the network of correlated residues of the polypeptide or mapping the network of correlated residues by using graph theory analysis and/or clustering tools.

In various embodiments, the invention provides a method of relating correlations between residues and residue networks of a polypeptide to a functional mechanism of the polypeptide comprising (a) determining correlated residues of the polypeptide by performing the method according to any of the preceding paragraphs; (b) mapping a network of correlated residues by using a spatial or distance constraint; or (c) mapping a network of correlated residues by using graph theory analysis and/or clustering tools, and (d) performing a dynamic cross correlation method or normal mode analysis of elastic network models to identify a correlation network due to domain movements within the polypeptide; (e) characterizing the networks of correlated residues identified in step (b,c) but not included in step (d); and (f) comparing the networks of steps (d) and (e) to experimental data regarding the functional mechanism, thereby relating correlations between residues of the polypeptide to the functional mechanism of the polypeptide.

In various embodiments, the invention provides a method of determining a network of correlated residues of a polypeptide comprising determining residue profiles or correlated residues of the polypeptide by performing the method according any of the preceding paragraphs; and mapping the network of correlated residues by using a spatial or distance constraint, thereby determining the network of correlated residues of the polypeptide or mapping the network of correlated residues by using graph theory analysis and/or clustering tools.

In various embodiments, the invention provides a method of relating correlations between residues and residue networks of a polypeptide to a functional mechanism of the polypeptide comprising (a) determining correlated residues of the polypeptide by performing the method according to any of the preceding paragraphs; (b) mapping a network of correlated residues by using a spatial or distance constraint; or (c) mapping the network of correlated residues by using graph theory analysis and clustering tools, and (d) performing a dynamic cross correlation method or normal mode analysis of elastic network models to identify a correlation network due to domain movements within the polypeptide; (e) characterizing the networks of correlated residues identified in step (b,c) but not included in step (d); and (f) comparing the networks of steps (d) and (e) to experimental data regarding the functional mechanism, thereby relating correlations between residues of the polypeptide to the functional mechanism of the polypeptide.

In various embodiments, the invention provides a method of engineering a polypeptide variant comprising determining correlations between residues of a first polypeptide by performing a method according to any preceding paragraph; choosing a mutational residue position of the first polypeptide based on the correlations between residues of the first polypeptide; and making the polypeptide variant comprising the sequence of the first polypeptide comprising a mutation at the mutational position of the first polypeptide, thereby engineering the polypeptide variant.

In various embodiments, the invention provides a method according to any preceding paragraph further comprising post-translationally modifying the polypeptide variant.

In various embodiments, the invention provides a method according to any preceding paragraph wherein the polypeptide variant comprises a nonnatural amino acid.

In various embodiments, the invention provides a method according to any preceding paragraph wherein the polypeptide variant has an altered property compared to a parent polypeptide, the property selected from the group consisting of enantioselectivity, substrate specificity, enzyme activity, thermal stability, pH stability, enzyme mechanism and product profile.

In various embodiments, the invention provides a method of engineering a nucleic acid encoding a polypeptide variant comprising determining polypeptide profiles or correlations between residues of a first polypeptide by performing a method according to any preceding paragraph; choosing a mutational residue position of the first polypeptide based on the correlations between residues of the first polypeptide; and synthesizing the nucleic acid encoding the polypeptide variant comprising the sequence of the first polypeptide comprising a mutation at the mutational position of the first polypeptide, thereby engineering the nucleic acid encoding the polypeptide variant.

In various embodiments, the invention provides a method of engineering a polypeptide ligand comprising determining polypeptide profiles or correlations between the residues of the polypeptide by performing a method according to any preceding paragraph; mapping a network of correlated residues using a spatial or distance constraint; identifying an allosteric site based on the network; designing a molecule to bind to the allosteric site; and synthesizing the molecule, thereby engineering the polypeptide ligand.

In various embodiments, the invention provides a method of engineering a polypeptide ligand comprising determining correlations between the residues of the polypeptide by performing a method according to any preceding paragraph; mapping a network of correlated residues using a spatial or distance constraint; and synthesizing a ligand, wherein a flexible architecture is engineered to maintain binding or activity for the enzyme, thereby engineering the polypeptide ligand.

In various embodiments, the invention provides a method of allosterically regulating a function of a polypeptide comprising determining polypeptide profiles or correlations between the residues of the polypeptide by performing a method according to any preceding paragraph; identifying an allosteric site based on the correlations; designing a ligand to bind the allosteric site; synthesizing the ligand; and contacting the ligand with the polypeptide, thereby regulating the function of the polypeptide.

In various embodiments, the invention provides a method of improving computational docking of a ligand to a polypeptide comprising determining polypeptide profiles or correlations between the residues of the polypeptide by performing a method according to any preceding paragraph; identifying flexible residues using the correlations; and using the flexible residues as inputs in a computational docking of the polypeptide, thereby improving computational docking of the ligand to the polypeptide.

In various embodiments, the invention provides a method of imprinting a conformational state onto a polypeptide comprising determining polypeptide profiles, conformational states or correlations between the residues of the polypeptide by performing a method according to any preceding paragraph; identifying flexible and framework residues using the correlations and/or protein profiles; using the conformational states as input to design polypeptide variants with a shifted distribution of conformations, thereby imprinting a conformational state onto the polypeptide with altered functionality.

In various embodiments, the invention provides a system for determining biopolymer or polypeptide profiles or correlations between residues of a polypeptide or relating correlations between residues and residue networks of a polypeptide to a functional mechanism of the polypeptide comprising a data storage device; a memory; and a processor comprising instructions for performing a method of determining biopolymer or polypeptide profiles or correlations between residues of a polypeptide or relating correlations between residues and residue networks of a polypeptide to a functional mechanism of the polypeptide, the method comprising a method according to any preceding paragraph.

In various embodiments, the invention provides a computer-readable medium comprising computer-executable instructions for performing a method of determining biopolymer or polypeptide profiles or correlations between residues of a polypeptide or relating correlations between residues and residue networks of a polypeptide to a functional mechanism of the polypeptide, the method comprising a method according to any preceding paragraph.

In various embodiments, the invention provides a polypeptide variant produced by a method according to any preceding paragraph.

In various embodiments, the invention provides a nucleic acid encoding the polypeptide of any preceding paragraph.

In various embodiments, the invention provides an expression vector comprising the nucleic acid of any preceding paragraph.

In various embodiments, the invention provides a host cell comprising the nucleic acid of any preceding paragraph.

In various embodiments, the invention provides a host cell comprising the expression vector of any preceding paragraph.

In various embodiments, the invention provides a method of defining geometric metrics as measuring a plane angle metric derived from an residue comprising measuring the angle between a first plane defined by a first set of atoms of the residue and a second plane defined by a second set of atoms.

In various embodiments, the invention provides a method of defining plane angles comprising fitting one or two planes to a set of atoms.

In various embodiments, the invention provides a method of defining geometric metrics comprising measuring the distance between any two atoms belonging to either the same or different residues.

In various embodiments, the invention provides a method according to any preceding paragraph further comprising using structural data snapshots derived from computational methods employing a Monte Carlo sampling technique or an experimental method.

In various embodiments, the invention provides a method according to any preceding paragraph wherein the experimental method is selected from the group consisting of NMR spectroscopy or X-ray crystallography.

Every reference, publication, patent application, issued patent, accession record, database and data file cited herein is expressly incorporated by reference in its entirety for all purposes and to the same extent as if each individual publication or reference was specifically and individually indicated to be incorporated by reference. As used herein, the articles "a", "an" and "the" mean "at least one" unless context clearly dictates otherwise. The conjunction "or" is not mutually exclusive, unless context clearly dictates otherwise.

Example

A 10 ns molecular dynamics simulation has been carried out on cutinase from *Fusarium solani* pis. The starting structure was derived from a high resolution crystal structure (pdb code: 1CEX.pdb). The saturated mutagensis data available (Brissos et. al., 2008; PEDS, 21(6):387) for this enzyme makes it a good example to highlight the data provided by the methods and applications described above.

Each residue in cutinase is in a unique environment in the 3-dimensional structure of this chiral biopolymer. This environment defines the likely conformational space available to the residue. The column stacked histogram plots in FIG. 4 panels A to D, present the results of the clustering analysis for every residue. The number of residue conformations for a residue, is indicated by the number of different colored sections for that residue. The respective populations for each residue conformation is shown by the height of the column. From these plots one can quickly identify which residues have discrete alternate residue conformations. This information is very useful for those skilled in the art. For example, many of the residues between 174 to 184, show on average more discrete conformations per residue. These residues are on a loop that forms an edge of the active site, that includes the catalytic aspartic acid (residue 175) in the cartoon representation of cutinase in FIG. 4 panel E (where residues 174 to 184 are colored magenta and all three catalytic residues are shown with sticks). The results of this analysis reveal that the residues in that region are not necessarily inherently flexible, but show preferred conformational substates, that are likely key to binding and catalysis. Additionally the column stacked plots, identify those residues that do not show any conformational preferences throughout the trajectory. These residues are usually solvent accessible, however if mobile residues are buried they are often key dynamic positions.

A representative structure for each residue conformation is available and can be superimposed on template backbone trace for a quick visualization of the conformational plasticity of a protein. An illustration of this data is provided in FIG. 5. Panel A shows the cartoon representation of cutinase ribbon with the side chains of the catalytic triad shown with magenta sticks. Shown in panel B are the representative residue conformations identified for cutinase superimposed on the structure shown in panel A. The first identified residue conformation is colored blue, then green, yellow, orange and red. As expected, for this hydrolase the figure in panel B shows that the residues in the core of this protein are predominately in a single conformation. This figure also shows the residues with alternate residue conformations as defined by this method. The increased plasticity at the surface and surrounding the active site cavity can easily be visualized and thus provides valuable structural information for those skilled in the art.

Figure 6:
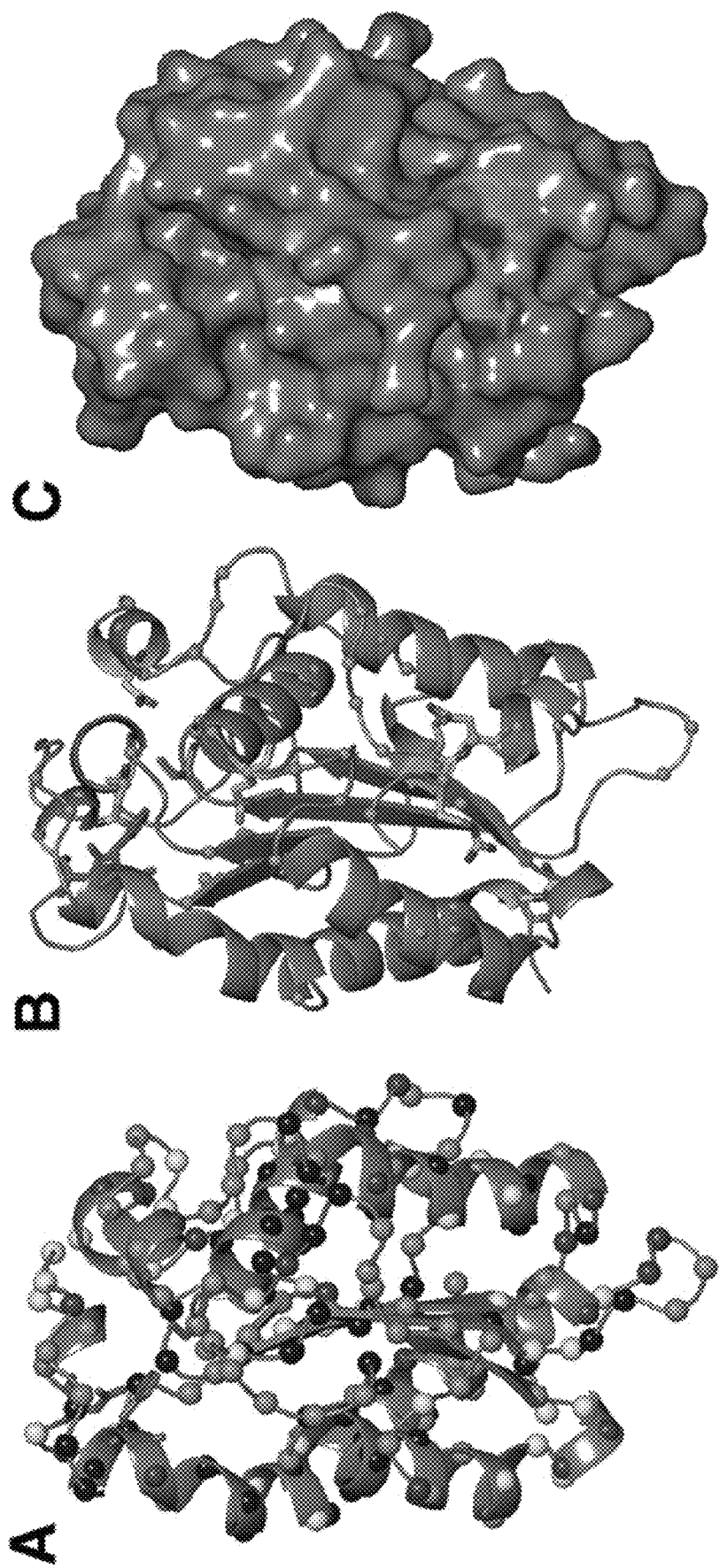
FIG. 6 is an example showing how the protein profiling data can be used. Details are provided in the examples section.

Based on a measure of the positional variance of the residue within its defined conformations and the overall number of frames where the residue is in any of these conformations a profile descriptor can be assigned. We can map this data onto the structure to provide a quick summary of the overall residue profile descriptions of the molecule, as shown in FIG. 6 panel A. Each CA atom of cutinase is colored according to a profiling method using only 4 bins, ranging from positionally rigid (blue) to conformationally diverse (red). With this information one can easily identify residues with alternate conformations that have limited mobility within their defined conformer positions.

One illustrative example of how the residue profiling information is used can be shown by using choosing to focus on polar residues with large side chains (amino acid types: N, Q, D, E, R and K). Generally these amino acid types are surface exposed and quite mobile and thus tolerant to mutation. If we use our profiling method to select a sub-set of these residues where they are profiled to be more positionally rigid (blue and green as shown in panel A) and observed in alternate conformations we obtain the following residues: R20, D21, E44, Q71, N152 and R208, shown as cyan colored sticks in panel B. All 7 of these automatically filtered residues are solvent accessible and are distributed throughout the surface of the enzyme. Note, that 3 of the 7 residues are in close proximity to the active site. The surface representation in panel C shows the protein in the identical orientation to that in panel B. Despite these residues having more than one defined residue conformation, they are identified by the profiling method as positionally rigid within those conformations and as such more likely to be of interest. The saturated mutagensis (Brissos et. al., 2008; PEDS, 21(6):387) data indicates that 5 of the 7 residues are very intolerant to mutations (where variant tolerance on a per residue basis was measured as the percentage of the 19 amino acids clones that have comparable wild-type or greater activity). Additionally, the average variant tolerance for all 7 residues (R20, D21, E44, Q71, N152 and R208) at 35% is lower than the overall tolerance average for the protein (45%). This is significant given the proportion of buried residues and their inherent sensitivity to mutation. Furthermore, the average variant tolerance for all of the large polar residue types (N, Q, D, E, R and K) is 49% despite the known importance of their electrostatic surface properties. In summary, these results show that the profiling data can be used to automatically identify distant residues that are more likely to be important for enzyme function.

As part of the protein profile, mobility for each residue was determined as described earlier and is correlated with the solvent accessible surface area (SASA) of every residue. In panel A of FIG. 7, each dot indicates the SASA and mobility for a specific residue of cutinase. Data points drawn in black indicate that out of 19 amino acids that have experimentally been used to replace the wild type residue 60% or more have full enzymatic activity (Brissos et. al., 2008; PEDS, 21(6):387). Points shown in green indicate full activity for 35 to 60% of mutants at this position those shown in red indicate 0 to 35% of active mutants. Cutoff values were chosen such that about equal amount of residues falls within each group. Squares in the respective colors indicate the average positions for the three data sets. Error bars up and left indicate the standard deviation, while error bars down and right show the standard error. The blue trendline is based on a linear regression analysis on all data points, the correlation coefficient between SASA and mobility is 0.54, which can be considered a moderate positive correlation. Panel B shows the same range of data divided into four quadrants, based on the average SASA and mobility value of all data points combined. Each quadrant can be assigned a status based on SASA and Mobility, which is indicated as EXP (exposed, larger than average surface area), BUR (buried, lower than average surface area), RIG (rigid, lower than average mobility) and MOB (mobile, larger than average mobility). The colored (scheme as above) numbers indicate the percentage of data points found within each of the four quadrants.

Figure 7A:
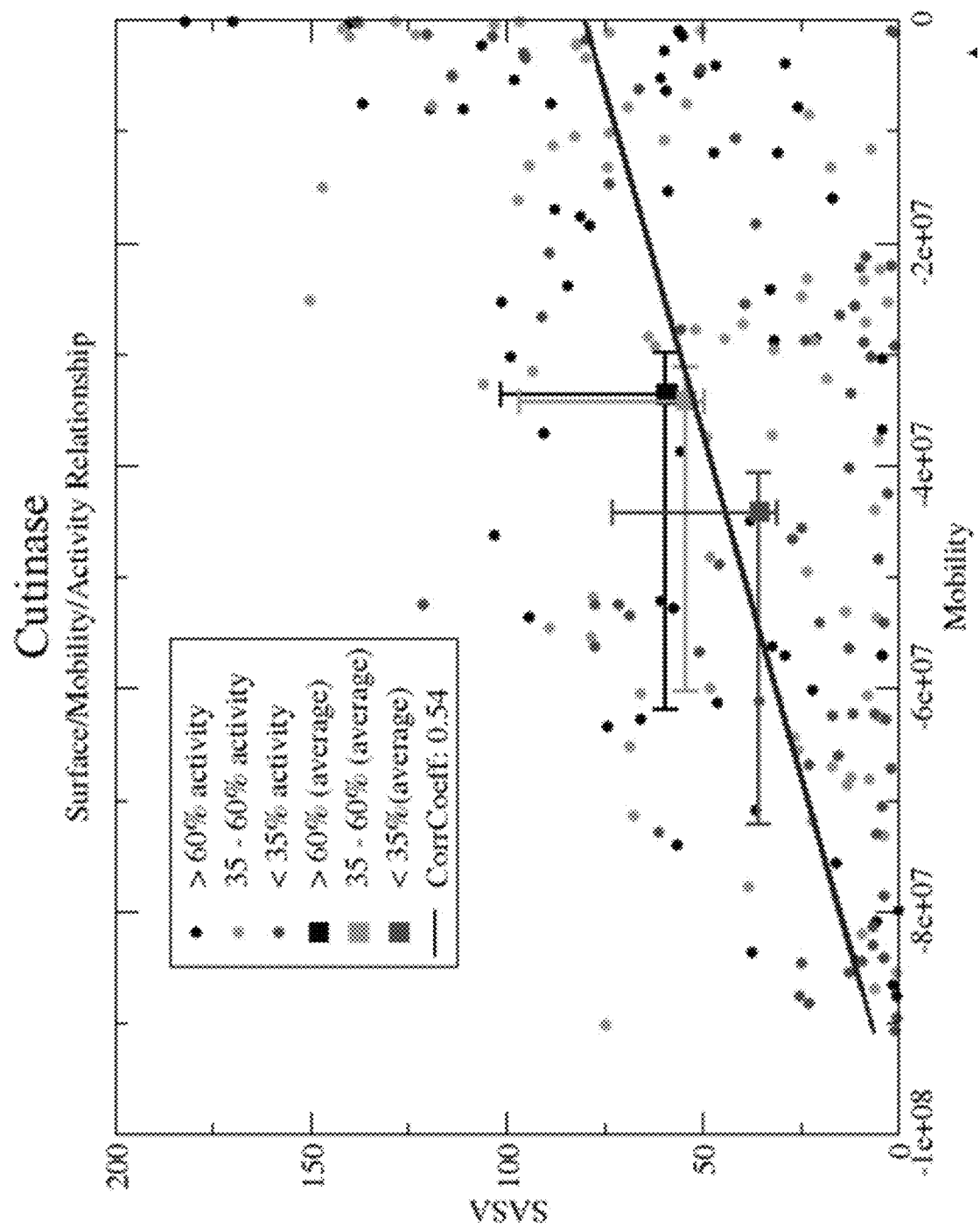
FIG. 7A-FIG. 7B shows the correlation between solvent accessible surface area of residues and their mobility as defined in the protein profile and their susceptibility to mutations. Details are provided in the examples section.
Figure 7B:
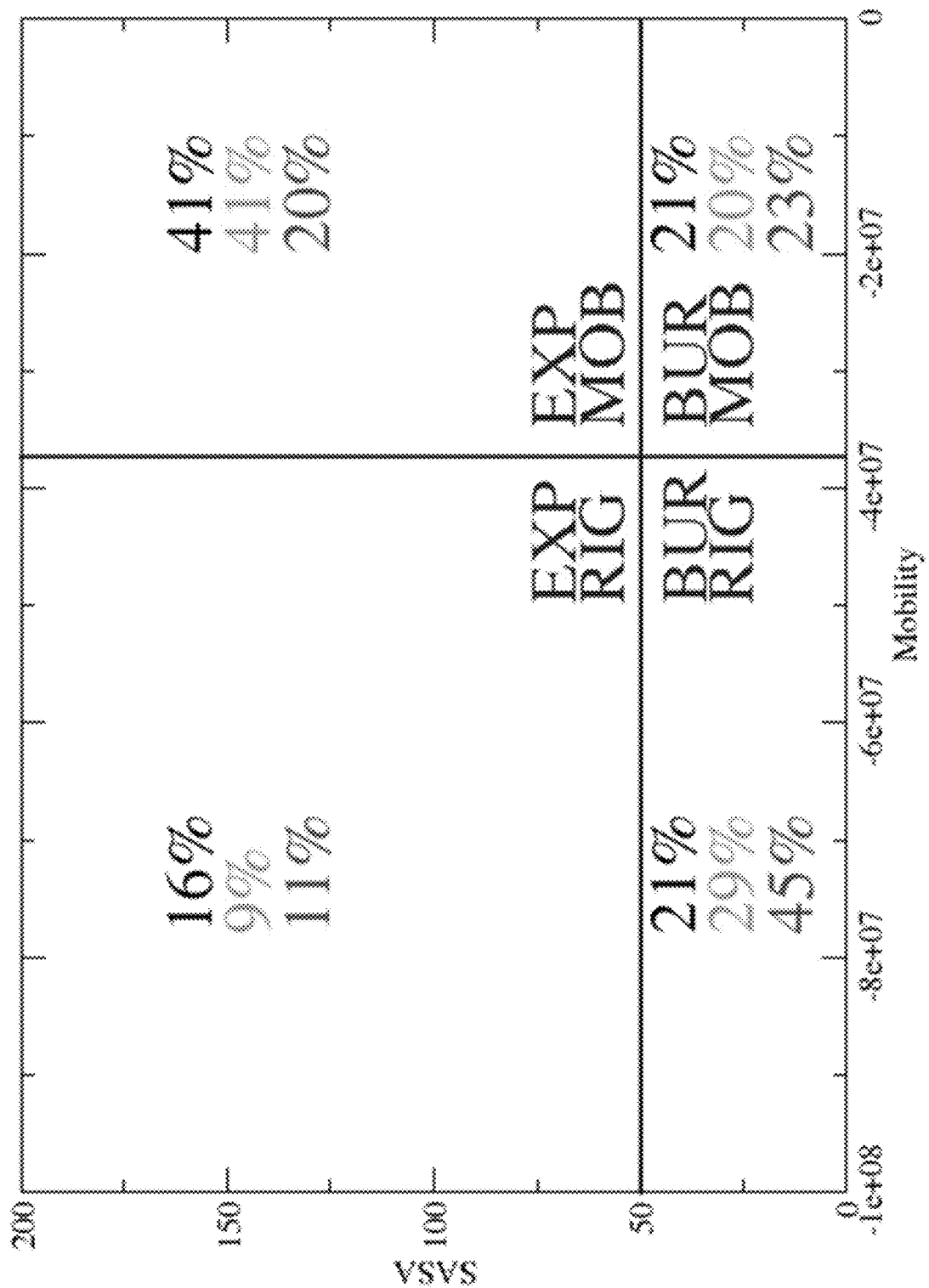

The data present in FIG. 7, shows, as expected, that a clear correlation could be established between the SASA and the mobility of each residue for the enzyme cutinase. This data set was broken down further (data not shown) on an amino acid basis, clearly showing different behavior for different types of amino acids. This clearly has to be considered when designing mutations at a specific position in the protein. Further, very clear evidence is shown that residues which are more susceptible to mutations are located in the lower left quadrant of the plot (BUR/RIG), while residues that tolerate mutations more easily are located on the upper right quadrant (EXP/MOB). In the example shown, 45% of residues for which less than 35% of mutations are active are located in the BUR/RIG quadrant, while only 21% of residues for which more than 60% of mutations are active are found in this region. In contrast to that the EXP/MOB quadrant includes 41% of tolerant residues and only 21% of susceptible residues. Plotting the residues the way shown in FIG. 7 clearly enables rational protein engineering decisions and helps to identify regions and residues in the protein, which are more likely to tolerate mutations from those that are potentially more sensitive. Finally, the positional mobility of a residue, also provides insight to the space available to a residue within the structure. The more positional variance observed for a residue the more likely that position will accommodate a larger side chain.

Figure 8A:
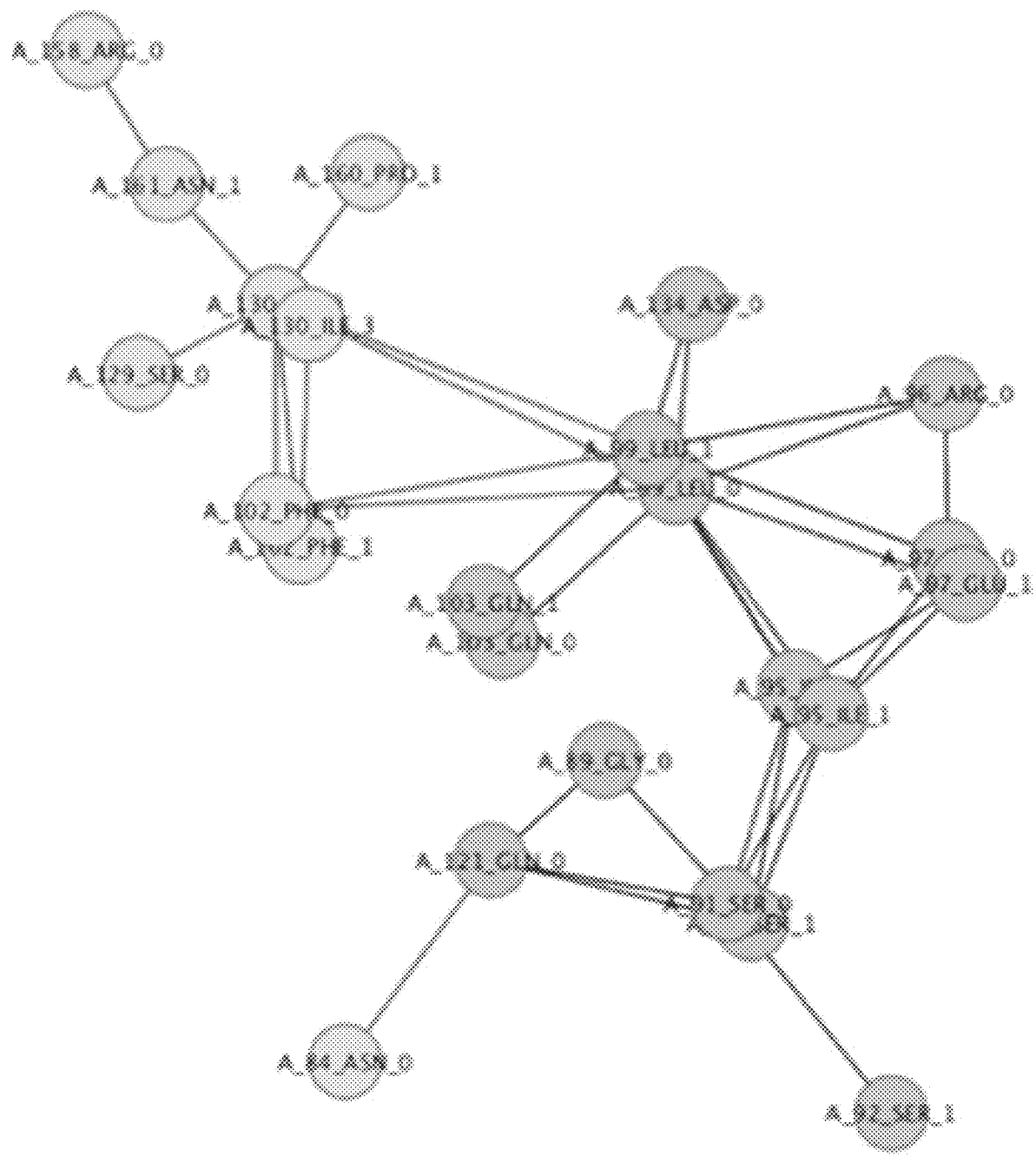
FIG. 8A-FIG. 8C is an example of how the residue network data can be used. Details are provided in the examples section.
Figure 8B:
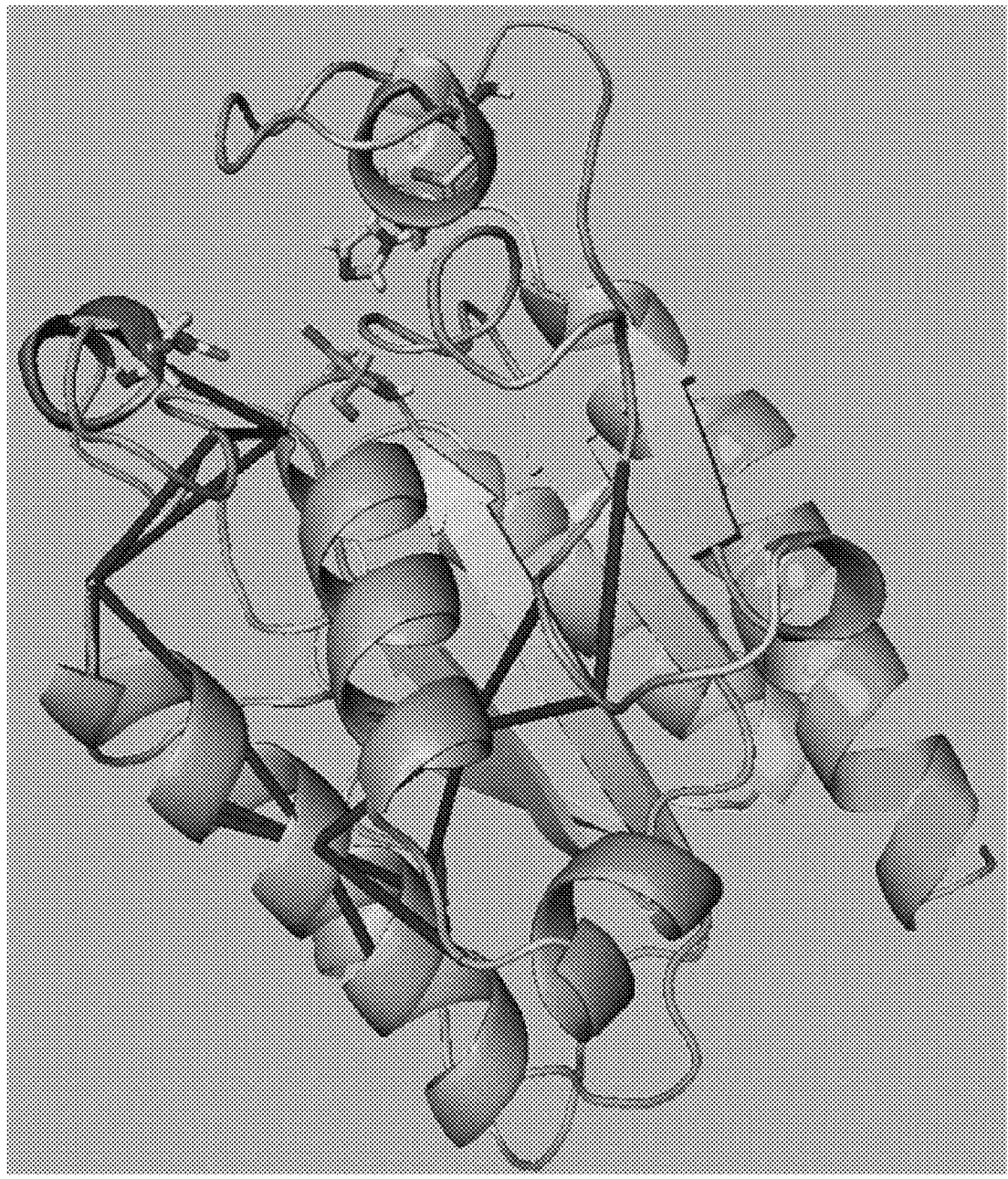
Figure 8C:
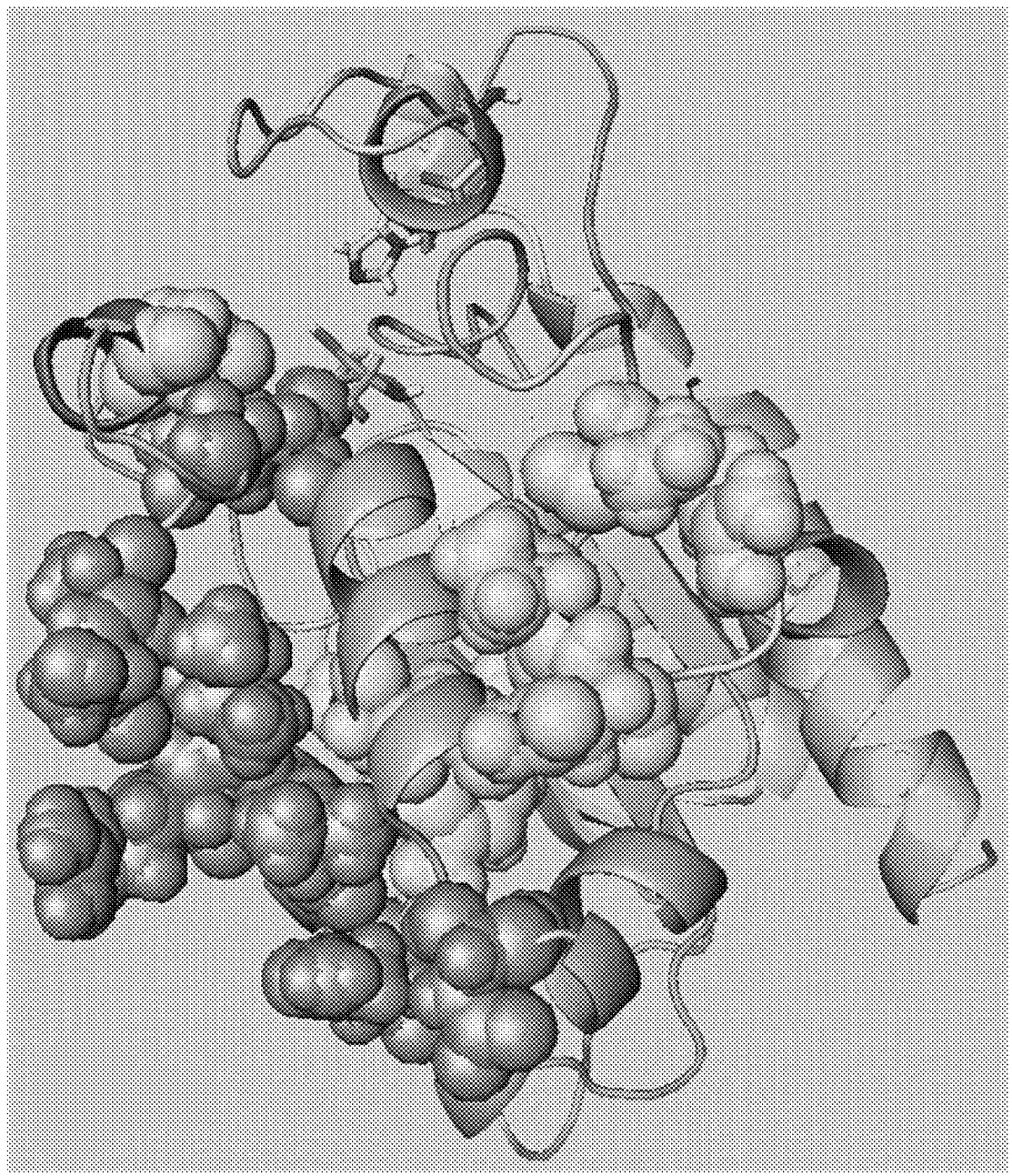

A correlated residue network observed in cutinase was identified using graphing techniques and the property of high interconnectivity of the pairwise residue correlation data. When we filter this graph with a distance cutoff of 4.5 Å (within van der Waals distance) we obtain the graph shown in FIG. 8 panel A. Each node (circle) represents a residue conformation and each edge represents a significant pairwise correlation between the two nodes. A residue may have more than one alternate conformation that is involved in network as shown. If we reduce this defined through space network to the level of the residue we can map this network on the structure by creating links between the CA atoms as shown in panel B. These networks can be used to identify residues distant to the active site that are likely to affect the binding and/or activity of this enzyme. The nodes in panel A are colored according to their mutational sensitivity, where nodes colored yellow are very sensitive to mutation as determined from the saturated mutagensis data provided in (Brissos et. al., 2008; PEDS, 21(6):387). All 7 of these sensitive residues display no activity for 70% of the variants at that position. In panel C you can see how these residues contact each other. The positionally sensitive residues (colored in yellow) interact primarily through side-chain interactions, while those colored pink interact through backbone interactions. The latter of which would be relatively less sensitive to mutagensis provided that there is space within the protein to accommodate a range of different side chains.

The average percentage of active clones for the sensitive residues (yellow) is 24% while the positionally tolerant residues average 65%. This example, shows that by identifying the dynamic correlated residue networks that involve active site residues one is able to gain insight about the allosteric effects of distant residues.

We claim:

1. A method of engineering a variant of a polypeptide, wherein the polypeptide comprises a plurality of residues, the method comprising:
   a) performing a molecular dynamics or Monte Carlo simulation to calculate a trajectory for a plurality of residue metrics using a three-dimensional atomic model of the polypeptide, wherein
      the plurality of residue metrics comprises a plane angle for a residue, or a backbone dihedral angle $\phi$ and $\Psi$ for a residue, or a distance vector r pointing from $C^\alpha$ to a terminal atom of a residue for each individual residue in the plurality of residues;
   b) determining at least one residue conformation for each corresponding residue in the plurality of residues, wherein
      the at least one residue conformation of a corresponding residue in the plurality of residues is obtained by clustering first conformation information for the corresponding residue in the trajectory, wherein the first conformation information comprises a subset of the plurality of residue metrics or the plurality of residue metrics for the corresponding residue;
   c) determining a conformational frequency of each of the at least one residue conformation of each residue in the plurality of residues;
   d) determining a variance in the residue conformation of each of the at least one residue conformation of each residue in the plurality of residues;
   e) assigning a mobility index to each respective residue in the plurality of residues based on the corresponding conformational frequency and the variance of each residue conformation in the at least one residue conformation of the respective residue; and
   f) engineering the variant of the polypeptide, wherein the variant of the polypeptide comprises the sequence of the polypeptide in which a first residue of the polypeptide has been substituted in the variant of the polypeptide for a different residue at least partly on the basis of the mobility index for the residue.

2. The method of claim 1 wherein a residue conformation in the at least one residue conformation of a residue in the plurality of residues is an off rotamer conformation of the residue.

3. The method of claim 1 wherein the clustering first conformation information for the corresponding residue comprises using a multidimensional clustering method.

4. The method of claim 1 wherein the polypeptide is selected from the group consisting of a structural protein, an antibody, an enzyme and a signaling protein.

5. The method of claim 1 wherein the simulation is performed using a Monte Carlo sampling technique.

6. The method of claim 1, wherein the first residue of the polypeptide has been substituted in the variant of the polypeptide for the different residue at least partly on the basis of (i) the mobility index for the residue and (ii) a solvent accessibility of the residue in the three-dimensional atomic model of the peptide.

7. The method of claim 1, wherein the simulation is a molecular dynamics simulation using the three-dimensional atomic model of the polypeptide.

* * * * *